United States Patent
Ford et al.

(10) Patent No.: US 6,392,019 B1
(45) Date of Patent: May 21, 2002

(54) ANTIBODIES SPECIFIC FOR EGF MOTIF PROTEINS

(76) Inventors: John Ford, 2763 S. Norfolk, #210, San Mateo, CA (US) 94403; George Yeung, 102 Magnolia La., Mountainview, CA (US) 94043

(*) Notice: Subject to any disclaimer, the term of this patent is extended or adjusted under 35 U.S.C. 154(b) by 0 days.

(21) Appl. No.: 09/363,316

(22) Filed: Jul. 28, 1999

Related U.S. Application Data

(63) Continuation-in-part of application No. 09/249,697, filed on Feb. 12, 1999, which is a continuation-in-part of application No. 08/968,800, filed on Nov. 22, 1997, now abandoned.

(51) Int. Cl.$^7$ .......................... C07K 2/00; C07K 14/00; C07K 16/00; C07K 16/18

(52) U.S. Cl. .................... 530/387.9; 530/300; 530/350; 530/387.1; 530/388.1; 530/389.1

(58) Field of Search ....................... 435/331; 530/387.1, 530/387.9, 388.1, 388.15, 389.1, 391.3, 300, 35 D, 388.23, 388.24, 389.2

(56) References Cited

U.S. PATENT DOCUMENTS

| | | | |
|---|---|---|---|
| 5,194,596 A | 3/1993 | Tisher et al. ................. 530/399 |
| 5,350,836 A | * 9/1994 | Kopchick et al. ............ 530/399 |
| 5,395,609 A | * 3/1995 | Stuttle et al. ............... 424/1.69 |
| 5,470,571 A | * 11/1995 | Herlyn et al. ............... 424/1.49 |

FOREIGN PATENT DOCUMENTS

| | | |
|---|---|---|
| WO | WO 92 19734 | 11/1992 |
| WO | WO 99 06553 | 2/1999 |
| WO | WO 99/46281 | 9/1999 |
| WO | WO 00/37638 | 6/2000 |
| WO | WO 00/39284 | 7/2000 |

OTHER PUBLICATIONS

Davis, C.G. The many faces of epidermal growth factor. New Biologist 2(5): 410–419, 1990.*
Connelly et al. Hepatic lipase deficiency. Crit Rev Clin Lab Sci 35(6): 547–572, 1998.*
Guadiz et al. Thrombin cleavage–independent deposition of fibrinogen in extracellular matrices. Blood 90(7): 2644–2653, 1997.*
Boukerche et al. Thrombospondin modulates melanoma––platelet interactions and melanoma tumour cell growth in vivo. Brit J Cancer 72:108–116, 1995.*
West et al. Correlation of vascular endothelial growth factor expression with fibroblast growth factor–8 expression and clinico–pathologic parameters in human prostate cancer. Brit J Cancer 85(4): 576–583, 2001.*
Riedel et al. Immunocytochemical localization of basic fibroblast growth factor in squamous cell carcinomas of the head and neck. Anticancer Res 21: 1873–1878, 2001.*
Chan et al. Prostate–specific antigen as a marker for prostatic cancer: a monoclonal and polyclonal immunoassay compared. Clin Chem 33(10): 1916–1920, 1987.*
Hayes et al. Circulating HER–2/erbB–2/c–neu (HER–2) extracellular domain as a prognostic factor in patients with metastatic breast cancer: cancer and leukemia group b study 8662. Clin Cancer Res 7: 2703–2711, 2001.*
Lissoni et al. The biological significance of soluble interleukin–2 receptors in solid tumors. Eur J Cancer 26(1): 33–36, 1990.*
Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Brenner, S.E. Errors in genome function. Trends in Genetics 15(4): 132–133, 1999.*
Bork et al. Go hunting in sequence databases but watch out for the traps. Trends in Genetics. 12(10): 425–427, 1996.*
Wells. J.A. Additivity of mutational effects in proteins. Biochemistry 29 (37): 8509–8517, 1990.*
Ngo et al. Computational complexity, protein structure prediction, and the Levinthal paradox. The Protein Folding Problem and Tertiary Structure Prediction, pp. 492–495, 1994.*
Benjamini and Leskowitz. Immunology: A Short Course. New York: John Wiley and Sons, 1991.*
McKnight et al., EGF–TM7: a novel subfamily of seven––transmembrane–region leukocyte cell–surface molecules, Immunology Today; 17(6): 283–287 (Jun. 1996).
Genebank Accession No.: R99817, yq69bll.rl Soares fetal liver spleen 1 NFLS Homo sapiens cDNA clone IMAGE: 201021 5' similar to SP:FBN1 HUMAN P35555 FIBRILLIN 1, mRNA sequence, deposited by Hillier et al., dated Sep. 14, 1995.
Genebank Accession No.: AA025649, ze85d03.rl Soares fetal heart NbHH19W Homo sapiens cDNA clone IMAGE: 365765 5', mRNA sequence, deposited by Hillier et al., dated Aug. 14, 1996.

(List continued on next page.)

Primary Examiner—Elizabeth Kemmerer
Assistant Examiner—Bridget E. Bunner
(74) Attorney, Agent, or Firm—Marshall, Gerstein, & Borun

(57) ABSTRACT

The present invention provides novel polynucleotides and proteins encoded by such polynucleotides, along with therapeutic, diagnostic and research utilities for these polynucleotides and proteins. In particular, the polypeptides of the invention comprise amino acid sequences with similarity to EGF-repeat domains.

9 Claims, 4 Drawing Sheets

OTHER PUBLICATIONS

Genebank Accession No.: AA436507, zv08c07.r1 Soares NhHMPu_S1 Homo sapiens cDNA clone IMAGE: 753036 5', mRNA sequence, deposited by Hillier et al., dated May 30, 1997.

Cunningham & Wells, High–Resolution Epitope Mapping of hGH–Receptor Interactions by Alanine–Scanning Mutagenesis, Science 244: 1081–1085 (Jun. 2, 1989).

Selander et al., $^1$H NMR Assignment and Secondary Structure of the $Ca^{2+}$–Free Form of the Amino–Terminal Epidermal Growth Factor like Domain in Coagulation Factor X, Biochemistry 29: 8111–8118 (1990).

Graves et al., Insight into E–selection/ligand interaction from the crystal structure and mutagenesis of the lec/EGF domains, Nature 367: 532–538 (Feb. 10, 1994).

* cited by examiner

```
Notch(C)   IDEC-SNP       CQNGGTC---D-VGSY-C-CPPGFT    GK---CE-N    D

10244(C)  -NECTM---       CQH----C  VNT-GSY-CKC-SG--   G--L-C       D
80                                  CRCFPGYT           GKT  CSQ     D
95        VNECGMKPRP      CQHR   C  VNTHGSYKCFCLS      GHMLMP       D
133       VNSRTCAMIN      CQYS   C  EDTEEGPQCLCPSS     GLRLAPN
175       IDECASGKVI      CPYNRRC   VNTFGSYYCKCHIGFE   LQYISGR
220       INECTMDSHT      CSHHANC   FNTQGSF CKCKQGYK   GNGRLCS

CD97(C)   V-EC-SG-Q--C-SS--C      -NTVGSY-CRCRPGW-P-PG-PN---  D

EGF(C)    NSDSECPLSHDGYCLHDGVCMYIEALDKYACNCVVGYI---GER--CQYRDLKWWELR
```

Figure 1

```
GGCTGGAGAA GAAACAGCAA GGGAGTCTGT GAAGCTACAT GCGAACCTGG
ATGTAAGTTT GGTGAGTGCG TGGGACCAAA CAAATGCAGA TGCTTTCCAG
GATACACCGG GAAAACCTGC AGTCAAGATG TGAATGAGTG TGGAATGAAA
CCCCGGCCAT GCCAACACAG ATGTGTGAAT ACACACGGAA GCTACAAGTG
CTTTTGCCTC AGTGGCCACA TGCTCATGCC AGATGCTACG TGTGTGAACT
CNAGGACATG TGCCATGATA AACTGTCAGT ATAGCTGTGA AGACACAGAA
SEQ ID NO: 1

GGCTGGAGAA GAAACAGCAA GGGAGTCTGT GAAGCTACAT GCGAACCTGG
ATGTAAGTTT GGTGAGTGCG TGGGACCAAA CAAATGCAGA TGCTTTCCAG
GATACACCGG GAAAACCTGC AGTCAAGATG TGAATGAGTG TGGAATGAAA
CCCCGGCCAT GCCAACACAG ATGTGTGAAT ACACACGGAA GCTACAAGTG
CTTTTGCCTC AGTGGCCACA TGCTCATGCC AGATGCTACG TGTGTGAACT
CNAGGACATG TGCCATGATA AACTGTCAGT ATAGCTGTGA AGACACAGAA
GAAGGGCCAC AGTGCCTGTG TCCATCCTCA GGACTCCGCC TGGCCCCAAA
TGGAAGAGAC TGTCTAGATA TTGATGAATG TGCCTCTGGT AAAGTCATCT
GTCCCTACAA TCGAAGATGT GTGAACACAT TTGGAAGCTA CTACTGCAAA
TGTCACATTG GTTTCGAACT GCAATATATC AGTGGACGAT ATGACTGTAT
AGATATAAAT GAATGTACTA TGGATAGCCA TACGTGCAGC CACCATGCCA
ATTGCTTCAA TACCCAAGGG TCCTTCAAGT GTAAATGCAA GCAGGGATAT
AAAGGCAATG GACTTCGGTG TTCTGCTATC CCTGAAAATT CTGTGAAGGA
AGTCCTCAGA GCACCTGGTA CCATCAAAGA CAGAATCAAG AAGTTGCTTG
CTCACAAAAA CAGCATGAAA AAGAAGGCAA AAATTAAAAA TGTTACCCCA
GAACCCACCA GGACTCCTAC CCCTAAGGTG AACTTGCAGC CCTTCAACTA
TGAAGAGATA GTTTCCAGAG GCGGGAACTC TCATGGAGGT AAAAAAGGGA
ATGAAGAGAA AATGAAAGAG GGGCTTGAGG ATGAGAAAAG AGAAGAGAAA
GCCCTGAAGA ATGACATAGA GGAGCAAGC CTGCGAGGAG ATGTGTTTTT
CCCTAAGGTG AATGAAGCAG GTGAATTCGG CCTGATTCTG GTCCAAAGGA
AAGCGCTAAC TTCCAAACTG GAACATAAAG ATTTAAATAT CTCGGTTGAC
TGCAGCTTCA ATCATGGGAT CTGTGACTGG AAACAGGATA GAGAAGATGA
TTTTGACTGG AATCCTGCTG ATCGAGATAA TGCTATTGGC TTCTATATGG
CAGTTCCGGC CTTGGCAGGT CACATGAAAG ACATTGGCCG ATTGAAACTT
CTCCTACCTG ACCTGCAACC CCAAAGCAAC TTCTGTTTGC TCTTTGATTA
CCGGCTGGCC GGAGACAAAG TCGGGAAACT TCGAGTGTTT GTGAAAAACA
GTAACAATGC CTGGCATGG GAGAAGACCA CGAGTGAGGA TGAAAAGTGG
AAGACAGGGA AAATTCAGTT GTATCAAGGA ACTGATGCTA CCAAAAGCAT
CATTTTTGAA GCAGAACGTG GCAAGGGCAA AACCGGCGAA ATCGCAGTGG
ATGGCGTCTT GCTTGTTTCA GGCTTATGTC CAGATAGCCT TTTATCTGTG
GANNNCTGAA TGGTACTATC TTTATATTTG ACTTTGTATG TCAGTTCCCT
GGTTTTTTTG ATATTGCATC ATAGGACCTC TGGCATTTTA AAATTACTAG
CTGAAAAATT G
SEQ ID NO: 2
```

FIGURE 2

GWRRNSKGVCEATCEPGCKFGECVGPNKCRCFPGYTGKTCSQDVNECGMKPRPCQHR
CVNTHGSYKCFCLSGHMLMPDATCVNSRTCAMINCQYSCEDTE
SEQ ID NO:3

GWRRNSKGVCEATCEPGCKFGECVGPNKCRCFPGYTGKTCSQDVNECGMKPRPCQHR
CVNTHGSYKCFCLSGHMLMPDATCVNSRTCAMINCQYSCEDTEEGPQCLCPSSGLRLAP
NGRDCLDIDECASGKVICPYNRRCVNTFGSYYCKCHIGFELQYISGRYDCIDINECTMDS
HTCSHHANCFNTQGSFKCKCKQGYKGNGLRCSAIPENSVKEVLRAPGTIKDRIKKLLAH
KNSMKKKAKIKNVTPEPTRTPTPKVNLQPFNYEEIVSRGGNSHGGKKGNEEKMKEGLE
DEKREEKALKNDIEERSLRGDVFFPKVNEAGEFGLILVQRKALTSKLEHKDLNISVDCSF
NHGICDWKQDREDDFDWNPADRDNAIGFYMAVPALAGHMKDIGRLKLLLPDLQPQSN
FCLLFDYRLAGDKVGKLRVFVKNSNNALAWEKTTSEDEKWKTGKIQLYQGTDATKSIIF
EAERGKGKTGEIAVDGVLLVSGLCPDSLLSVDDXMVLSLYLTLYVSSLVFLILHHRTSGI
LKLLAEKL
SEQ ID NO:4

FIGURE 3

ACTAGTGATTCCATCCTAATACGACTCACTATAGGGCTCGAGCGGCCGCCCGGGCAGGTCTGCAGGACAGCACCGGTA
ACTGCGAGTGGAGCGGAGAACCCGAGCGGCTGAGGAGGAAGGAGGAGGGCGGCGCTTAGCTGCCTGGAGCTTCCGGCGCC
CTCCCGAGGGGGCTCAGGAGGTGGCAGGTGGTTTCGGAACGCGGCCAGTGCCTGCTACGGGTTGTTAGCACGGCATCAGCTGG
CTCCCCTGGGTGGCAGGTGTTTCGGAACGCGGCCAGTGCCTGCTACGGGTTGTTAGCATCGGCACGTCAGCTGG
GGTCTGTCACTATGGAACTAAACTGGCCTGCTGCTACGGTGGGACCAAACAAATGAGATGCTTTCCAGGATACACACGGAAGCTACATGCG
AACCTGATGTAAGTTTGGTGAGTGCGTGGGACCAAACAAATGAGATGCTTTCCAGGATACACACGGAAGCTACATGCG
CAAGATGTGAATGAGTGTGGAATGAAACCCGGCCATGCCAACACAGATCTGTGAATACACAGGAAGCTACAAGTGCTT
TGCCTCAGTGGCCACATGCTCATGCCAGATGCTACGTGTGTCCATCCTCAGGACTCCGGAACTGCCATGATAAACTGTCAGTATA
GCTGTGAAGACACAGAAGGGCCACAGTGCCTCTGGTAAAGTCATCTGTCTGCCTACCGTGTCCCCAAATGGAAGAGACTGT
CTAGATATTGATGAATGTGCCTCTGGTAAAGTCATCTGTCCCTACAATCGAAGATGTGTGAACACATTTGGAAGCTACTA
CTGCAAATGTCACATTGGTTTCGAACTGCAATATATCAGTGACGATATGACTGACATGACTGTATAGATATAAATGAATGTACTATGG
ATAGCCATACGTGCAGCCACCATGCCAATTGCTTCAATACCCAAGGGTCCTTCAAGTGTAAATGCAAGCAGGATATAAA
GGCAATGGACTTCCGTTCTGTCTACAAAAACAGCATGAAAAAGAAGGCAAAAATTAAAAATGTTACCCAGAACCACCAGA
AATCAAGAAGTTGCTTGCTCACAAAAACAGCATGAAAAAGAAGGCAAAAATTAAAAATGTTACCCAGAACCACCAGA
CTCCTACCCTAAGTGAACTTGCAGCCCTTCAACTTGCCTATGAGAGAGAAAGCCCTGAAGAATGACWTAGAGGA
AAAGGGAATGAAGAGAAAATGAAGAGATGTGTTTTCCTAAGGCTTGAGGATGGAATGAAGACAGGTGAATTCGGCCTGATTCTGGTCAAAGGAAAG
CGCTAACTTCCAAACTGCAACATAAAGATTTAAATATCTCGGTTGACTGCAGCTTCAATCATGGAATCTGACTGGAAA
CAGGATAGAAGAAGATGATTTTGACTGGAATCCTGCTGAATCTTTATATTTGACTTTGTATGCAGTTCCGGCCTT
GGCAGGTCACAAGAAAGATGATTTGGCCGATTGAAACTTCTCCTACCTGACCTGTTTGTGAAAAACAGTAACAATGCCTGGCATGGAG
TTGATTACCCCGTCCGGAGACAAAGTGGAAGACAGGGACAAAGTGGAAGAACCGGAGAACTGATGCTACCAAAAGCATCAT
AAGACCACCAGTGAGGATGAAAGTGGAAGACAGGGACAAAACCGGCGAAATCGCAGTGATGCGTCTTGCTTGTCAGTTCCCTGCTTTTTTGATA
TTTTGAAGCAGAACGTGCAAAGTCGGAAGACAGGGACAAAACCGGCGAAATCGCAGTGATGCGTCTTGCTTGTCAGTTCCCTGCTTTTTTGATA
ATAGCCTTTATCTGTGATGACTGAAGTTACTATCTTATATTGACTTTGTATGTCAGTTCCCTGCTTTTTTGATA
TTGSATCATAGGACCTCTGGCATTTTAAAATTACTAAGCTGCAATATTTGCTTAAATATCATATCACTGTATCTCTCCAGTCAGTTGTATAAGTAAGTGATGA
TGCCTTTTMTTGTATAAGATATGCCAATATTGCAGGTTTATTCCCCTCCAGTACTATCTCAGTCATTTTCTCAATCTTTC
CACATTATATTATAAATATGGAAATGTCAGTTAATAGAHAAAAAAAAGCACAGACAAATGTTAACTGTTGACTCTTATGATAGTTTT
GCTTCTCTGCAACATTTCTAGAAATAGAHAAAAAAAAGCACAGACAAATGTTAACTGTTGACTCTTATGATAGTTTT
TGGAAACTATGACATCAAAGATAGACTTTTGCCTAAGTGGCTTAGCTGGGTCTTTCATAGCCAAACTTGTATATTTAAAT
TCTTTGTAATAATAATATCCAAATCATCAAAAAAAAAAAAAAAAA
SEQ ID NO:5

FIGURE 4

MPLPWSLALPLLLPWVAGGFGNAASARHHGLLASARQPGVCHYGTKLACCYGWRRNSKGVCEATCEPGCKFGECVGPNKC
RCFPGYTGKTCSQDVNECGMKPRPCQHRCVNTHGSYKCFCLSGHMLMPDATCVNSRTCAMINCQYSCEDTEEGPQCLCPS
SGLRLAPNGRDCLDIDECASGKVICPYNRRCVNTFGSYYCKCHIGFELQYISGRYDCIDINECTMDSHTCSHHANCFNTQ
GSFKCKCKQGYKGNGLRCSAIPENSVKEVLRAPGTIKDRIKKLLAHKNSMKKKAKIKNVTPEPTRIPTPKVNLQPFNYEE
IVSRGGNSHGGKKGNEEKMKEGLEDEKREEKALKNDXEERSLRGDVFFPKVNEAGEFGLILVQRKALTSKLEHKDLNISV
DCSFNHGICDWKQDREDDFDWNPADRDNAIGFYMAVPALAGHKKDIGRLKLLLPDLQPQSNFCLLFDYRLAGDKVGKLRV
FVKNSNNALAWEKTTSEDEKWKTGKIQLYQGTDATKSIIFEAERGKGKTGELAVDGVLLVSGLCPDSLLSVDD
SEQ ID NO: 6

FIGURE 5

SEQUENCE LISTING

```
<160> NUMBER OF SEQ ID NOS: 24

<210> SEQ ID NO 1
<211> LENGTH: 300
<212> TYPE: DNA
<213> ORGANISM: Homo sapiens
<220> FEATURE:
<221> NAME/KEY: CDS
<222> LOCATION: (1)...(300)
<221> NAME/KEY: misc_feature
<222> LOCATION: (84)
<223> OTHER INFORMATION: Xaa = any amino acid
<221> NAME/KEY: misc_feature
<222> LOCATION: (252)
<223> OTHER INFORMATION: n = a, g, c o r t

<400> SEQUENCE: 1 ggc tgg aga aga aac agc aag gga gtc tgt g aa gct aca tgc gaa cct         48
Gly Trp Arg Arg Asn Ser Lys Gly Val Cys G lu Ala Thr Cys Glu Pro
 1               5                  10                  15 gga tgt aag ttt ggt gag tgc gtg gga cca a ac aaa tgc aga tgc ttt         96
Gly Cys Lys Phe Gly Glu Cys Val Gly Pro A sn Lys Cys Arg Cys Phe
                20                  25                  30 cca gga tac acc ggg aaa acc tgc agt caa g at gtg aat gag tgt gga        144
Pro Gly Tyr Thr Gly Lys Thr Cys Ser Gln A sp Val Asn Glu Cys Gly
             35                  40                  45 atg aaa ccc cgg cca tgc caa cac aga tgt g tg aat aca cac gga agc        192
Met Lys Pro Arg Pro Cys Gln His Arg Cys V al Asn Thr His Gly Ser
         50                  55                  60 tac aag tgc ttt tgc ctc agt ggc cac atg c tc atg cca gat gct acg        240
Tyr Lys Cys Phe Cys Leu Ser Gly His Met L eu Met Pro Asp Ala Thr
 65                  70                  75                  80 tgt gtg aac tcn agg aca tgt gcc atg ata a ac tgt cag tat agc tgt        288
Cys Val Asn Xaa Arg Thr Cys Ala Met Ile A sn Cys Gln Tyr Ser Cys
                 85                  90                  95 gaa gac aca gaa                                                         300
Glu Asp Thr Glu
            100
```

```
<210> SEQ ID NO 2
<211> LENGTH: 1611
<212> TYPE: DNA
<213> ORGANISM: Homo sapiens
<220> FEATURE:
<221> NAME/KEY: CDS
<222> LOCATION: (1)...(1506)
<221> NAME/KEY: misc_feature
<222> LOCATION: (84)
<223> OTHER INFORMATION: Xaa = any amino acid
<221> NAME/KEY: misc_feature
<222> LOCATION: (252)
<223> OTHER INFORMATION: n = a, g, c o r t
<221> NAME/KEY: misc_feature
<222> LOCATION: (501)
<223> OTHER INFORMATION: Xaa = any amino acid
<221> NAME/KEY: misc_feature
<222> LOCATION: (502)
<223> OTHER INFORMATION: Xaa = any amino acid
<221> NAME/KEY: misc_feature
<222> LOCATION: (1503-1505)
<223> OTHER INFORMATION: n = a, g, c o r t

<400> SEQUENCE: 2
```

| | | | | | | | | | | | | | | | | |
|---|---|---|---|---|---|---|---|---|---|---|---|---|---|---|---|---|
| ggc | tgg | aga | aga | aac | agc | aag | gga | gtc | tgt | g aa | gct | aca | tgc | gaa | cct | 48 |
| Gly | Trp | Arg | Arg | Asn | Ser | Lys | Gly | Val | Cys | G lu | Ala | Thr | Cys | Glu | Pro | |
| 1 | | | | 5 | | | | | 10 | | | | | 15 | | |
| gga | tgt | aag | ttt | ggt | gag | tgc | gtg | gga | cca | a ac | aaa | tgc | aga | tgc | ttt | 96 |
| Gly | Cys | Lys | Phe | Gly | Glu | Cys | Val | Gly | Pro | A sn | Lys | Cys | Arg | Cys | Phe | |
| | | 20 | | | | | 25 | | | | | 30 | | | | |
| cca | gga | tac | acc | ggg | aaa | acc | tgc | agt | caa | g at | gtg | aat | gag | tgt | gga | 144 |
| Pro | Gly | Tyr | Thr | Gly | Lys | Thr | Cys | Ser | Gln | A sp | Val | Asn | Glu | Cys | Gly | |
| | | | 35 | | | | | 40 | | | | | 45 | | | |
| atg | aaa | ccc | cgg | cca | tgc | caa | cac | aga | tgt | g tg | aat | aca | cac | gga | agc | 192 |
| Met | Lys | Pro | Arg | Pro | Cys | Gln | His | Arg | Cys | V al | Asn | Thr | His | Gly | Ser | |
| 50 | | | | | 55 | | | | | 60 | | | | | | |
| tac | aag | tgc | ttt | tgc | ctc | agt | ggc | cac | atg | c tc | atg | cca | gat | gct | acg | 240 |
| Tyr | Lys | Cys | Phe | Cys | Leu | Ser | Gly | His | Met | L eu | Met | Pro | Asp | Ala | Thr | |
| 65 | | | | 70 | | | | | 75 | | | | | 80 | | |
| tgt | gtg | aac | tcn | agg | aca | tgt | gcc | atg | ata | a ac | tgt | cag | tat | agc | tgt | 288 |
| Cys | Val | Asn | Xaa | Arg | Thr | Cys | Ala | Met | Ile | A sn | Cys | Gln | Tyr | Ser | Cys | |
| | | | | 85 | | | | | 90 | | | | | 95 | | |
| gaa | gac | aca | gaa | gaa | ggg | cca | cag | tgc | ctg | t gt | cca | tcc | tca | gga | ctc | 336 |
| Glu | Asp | Thr | Glu | Glu | Gly | Pro | Gln | Cys | Leu | C ys | Pro | Ser | Ser | Gly | Leu | |
| | | | 100 | | | | | 105 | | | | | 110 | | | |
| cgc | ctg | gcc | cca | aat | gga | aga | gac | tgt | cta | g at | att | gat | gaa | tgt | gcc | 384 |
| Arg | Leu | Ala | Pro | Asn | Gly | Arg | Asp | Cys | Leu | A sp | Ile | Asp | Glu | Cys | Ala | |
| | | | | 115 | | | | | 120 | | | | | 125 | | |
| tct | ggt | aaa | gtc | atc | tgt | ccc | tac | aat | cga | a ga | tgt | gtg | aac | aca | ttt | 432 |
| Ser | Gly | Lys | Val | Ile | Cys | Pro | Tyr | Asn | Arg | A rg | Cys | Val | Asn | Thr | Phe | |
| | 130 | | | | | 135 | | | | | 140 | | | | | |
| gga | agc | tac | tac | tgc | aaa | tgt | cac | att | ggt | t tc | gaa | ctg | caa | tat | atc | 480 |
| Gly | Ser | Tyr | Tyr | Cys | Lys | Cys | His | Ile | Gly | P he | Glu | Leu | Gln | Tyr | Ile | |
| 145 | | | | | 150 | | | | | 155 | | | | | 160 | |
| agt | gga | cga | tat | gac | tgt | ata | gat | ata | aat | g aa | tgt | act | atg | gat | agc | 528 |
| Ser | Gly | Arg | Tyr | Asp | Cys | Ile | Asp | Ile | Asn | G lu | Cys | Thr | Met | Asp | Ser | |
| | | | | 165 | | | | | 170 | | | | | 175 | | |
| cat | acg | tgc | agc | cac | cat | gcc | aat | tgc | ttc | a at | acc | caa | ggg | tcc | ttc | 576 |
| His | Thr | Cys | Ser | His | His | Ala | Asn | Cys | Phe | A sn | Thr | Gln | Gly | Ser | Phe | |
| | | | 180 | | | | | 185 | | | | | 190 | | | |
| aag | tgt | aaa | tgc | aag | cag | gga | tat | aaa | ggc | a at | gga | ctt | cgg | tgt | tct | 624 |
| Lys | Cys | Lys | Cys | Lys | Gln | Gly | Tyr | Lys | Gly | A sn | Gly | Leu | Arg | Cys | Ser | |
| | | | | 195 | | | | | 200 | | | | | 205 | | |
| gct | atc | cct | gaa | aat | tct | gtg | aag | gaa | gtc | c tc | aga | gca | cct | ggt | acc | 672 |
| Ala | Ile | Pro | Glu | Asn | Ser | Val | Lys | Glu | Val | L eu | Arg | Ala | Pro | Gly | Thr | |

```
                 210                 215                 220
atc aaa gac aga atc aag aag ttg ctt gct c ac aaa aac agc atg aaa      720
Ile Lys Asp Arg Ile Lys Lys Leu Leu Ala H is Lys Asn Ser Met Lys
225                 230                 235                 240 aag aag gca aaa att aaa aat gtt acc cca g aa ccc acc agg act cct      768
Lys Lys Ala Lys Ile Lys Asn Val Thr Pro G lu Pro Thr Arg Thr Pro
                245                 250                 255 acc cct aag gtg aac ttg cag ccc ttc aac t at gaa gag ata gtt tcc      816
Thr Pro Lys Val Asn Leu Gln Pro Phe Asn T yr Glu Glu Ile Val Ser
                260                 265                 270 aga ggc ggg aac tct cat gga ggt aaa aaa g gg aat gaa gag aaa atg     864
Arg Gly Gly Asn Ser His Gly Gly Lys Lys G ly Asn Glu Glu Lys Met
                275                 280                 285 aaa gag ggg ctt gag gat gag aaa aga gaa g ag aaa gcc ctg aag aat     912
Lys Glu Gly Leu Glu Asp Glu Lys Arg Glu G lu Lys Ala Leu Lys Asn
290                 295                 300 gac ata gag gag cga agc ctg cga gga gat g tg ttt ttc cct aag gtg     960
Asp Ile Glu Glu Arg Ser Leu Arg Gly Asp V al Phe Phe Pro Lys Val
305                 310                 315                 320 aat gaa gca ggt gaa ttc ggc ctg att ctg g tc caa agg aaa gcg cta    1008
Asn Glu Ala Gly Glu Phe Gly Leu Ile Leu V al Gln Arg Lys Ala Leu
                325                 330                 335 act tcc aaa ctg gaa cat aaa gat tta aat a tc tcg gtt gac tgc agc    1056
Thr Ser Lys Leu Glu His Lys Asp Leu Asn I le Ser Val Asp Cys Ser
                340                 345                 350 ttc aat cat ggg atc tgt gac tgg aaa cag g at aga gaa gat gat ttt    1104
Phe Asn His Gly Ile Cys Asp Trp Lys Gln A sp Arg Glu Asp Asp Phe
                355                 360                 365 gac tgg aat cct gct gat cga gat aat gct a tt ggc ttc tat atg gca    1152
Asp Trp Asn Pro Ala Asp Arg Asp Asn Ala I le Gly Phe Tyr Met Ala
370                 375                 380 gtt ccg gcc ttg gca ggt cac atg aaa gac a tt ggc cga ttg aaa ctt    1200
Val Pro Ala Leu Ala Gly His Met Lys Asp I le Gly Arg Leu Lys Leu
385                 390                 395                 400 ctc cta cct gac ctg caa ccc caa agc aac t tc tgt ttg ctc ttt gat    1248
Leu Leu Pro Asp Leu Gln Pro Gln Ser Asn P he Cys Leu Leu Phe Asp
                405                 410                 415 tac cgg ctg gcc gga gac aaa gtc ggg aaa c tt cga gtg ttt gtg aaa    1296
Tyr Arg Leu Ala Gly Asp Lys Val Gly Lys L eu Arg Val Phe Val Lys
                420                 425                 430 aac agt aac aat gcc ctg gca tgg gag aag a cc acg agt gag gat gaa    1344
Asn Ser Asn Asn Ala Leu Ala Trp Glu Lys T hr Thr Ser Glu Asp Glu
                435                 440                 445 aag tgg aag aca ggg aaa att cag ttg tat c aa gga act gat gct acc    1392
Lys Trp Lys Thr Gly Lys Ile Gln Leu Tyr G ln Gly Thr Asp Ala Thr
450                 455                 460 aaa agc atc att ttt gaa gca gaa cgt ggc a ag ggc aaa acc ggc gaa    1440
Lys Ser Ile Ile Phe Glu Ala Glu Arg Gly L ys Gly Lys Thr Gly Glu
465                 470                 475                 480 atc gca gtg gat ggc gtc ttg ctt gtt tca g gc tta tgt cca gat agc    1488
Ile Ala Val Asp Gly Val Leu Leu Val Ser G ly Leu Cys Pro Asp Ser
                485                 490                 495 ctt tta tct gtg gan nnc tgaatggtac tatctttata t ttgactttg           1536
Leu Leu Ser Val Xaa Xaa
                500 tatgtcagtt ccctggtttt tttgatattg catcatagga cctctggcat t ttaaaatta  1596 ctagctgaaa aattg                                                    1611
```

```
<210> SEQ ID NO 3
<211> LENGTH: 100
<212> TYPE: PRT
<213> ORGANISM: Homo sapiens

<400> SEQUENCE: 3

Gly Trp Arg Arg Asn Ser Lys Gly Val Cys G lu Ala Thr Cys Glu Pro
 1               5                  10                  15

Gly Cys Lys Phe Gly Glu Cys Val Gly Pro A sn Lys Cys Arg Cys Phe
            20                  25                  30

Pro Gly Tyr Thr Gly Lys Thr Cys Ser Gln A sp Val Asn Glu Cys Gly
        35                  40                  45

Met Lys Pro Arg Pro Cys Gln His Arg Cys V al Asn Thr His Gly Ser
50                  55                  60

Tyr Lys Cys Phe Cys Leu Ser Gly His Met L eu Met Pro Asp Ala Thr
65                  70                  75                  80

Cys Val Asn Ser Arg Thr Cys Ala Met Ile A sn Cys Gln Tyr Ser Cys
                85                  90                  95

Glu Asp Thr Glu
            100

<210> SEQ ID NO 4
<211> LENGTH: 537
<212> TYPE: PRT
<213> ORGANISM: Homo sapiens
<220> FEATURE:
<221> NAME/KEY: misc_feature
<222> LOCATION: (503)
<223> OTHER INFORMATION: Xaa = any amino acid

<400> SEQUENCE: 4

Gly Trp Arg Arg Asn Ser Lys Gly Val Cys G lu Ala Thr Cys Glu Pro
 1               5                  10                  15

Gly Cys Lys Phe Gly Glu Cys Val Gly Pro A sn Lys Cys Arg Cys Phe
            20                  25                  30

Pro Gly Tyr Thr Gly Lys Thr Cys Ser Gln A sp Val Asn Glu Cys Gly
        35                  40                  45

Met Lys Pro Arg Pro Cys Gln His Arg Cys V al Asn Thr His Gly Ser
50                  55                  60

Tyr Lys Cys Phe Cys Leu Ser Gly His Met L eu Met Pro Asp Ala Thr
65                  70                  75                  80

Cys Val Asn Ser Arg Thr Cys Ala Met Ile A sn Cys Gln Tyr Ser Cys
                85                  90                  95

Glu Asp Thr Glu Glu Gly Pro Gln Cys Leu C ys Pro Ser Ser Gly Leu
            100                 105                 110

Arg Leu Ala Pro Asn Gly Arg Asp Cys Leu A sp Ile Asp Glu Cys Ala
            115                 120                 125

Ser Gly Lys Val Ile Cys Pro Tyr Asn Arg A rg Cys Val Asn Thr Phe
        130                 135                 140

Gly Ser Tyr Tyr Cys Lys Cys His Ile Gly P he Glu Leu Gln Tyr Ile
145                 150                 155                 160

Ser Gly Arg Tyr Asp Cys Ile Asp Ile Asn G lu Cys Thr Met Asp Ser
                165                 170                 175

His Thr Cys Ser His Ala Asn Cys Phe A sn Thr Gln Gly Ser Phe
            180                 185                 190

Lys Cys Lys Cys Lys Gln Gly Tyr Lys Gly A sn Gly Leu Arg Cys Ser
            195                 200                 205
```

```
Ala Ile Pro Glu Asn Ser Val Lys Glu Val Leu Arg Ala Pro Gly Thr
    210                 215                 220

Ile Lys Asp Arg Ile Lys Lys Leu Leu Ala His Lys Asn Ser Met Lys
225                 230                 235                 240

Lys Lys Ala Lys Ile Lys Asn Val Thr Pro Glu Pro Thr Arg Thr Pro
                245                 250                 255

Thr Pro Lys Val Asn Leu Gln Pro Phe Asn Tyr Glu Glu Ile Val Ser
            260                 265                 270

Arg Gly Gly Asn Ser His Gly Gly Lys Lys Gly Asn Glu Glu Lys Met
        275                 280                 285

Lys Glu Gly Leu Glu Asp Glu Lys Arg Glu Glu Lys Ala Leu Lys Asn
    290                 295                 300

Asp Ile Glu Glu Arg Ser Leu Arg Gly Asp Val Phe Phe Pro Lys Val
305                 310                 315                 320

Asn Glu Ala Gly Glu Phe Gly Leu Ile Leu Val Gln Arg Lys Ala Leu
                325                 330                 335

Thr Ser Lys Leu Glu His Lys Asp Leu Asn Ile Ser Val Asp Cys Ser
            340                 345                 350

Phe Asn His Gly Ile Cys Asp Trp Lys Gln Asp Arg Glu Asp Asp Phe
        355                 360                 365

Asp Trp Asn Pro Ala Asp Arg Asp Asn Ala Ile Gly Phe Tyr Met Ala
    370                 375                 380

Val Pro Ala Leu Ala Gly His Met Lys Asp Ile Gly Arg Leu Lys Leu
385                 390                 395                 400

Leu Leu Pro Asp Leu Gln Pro Gln Ser Asn Phe Cys Leu Leu Phe Asp
                405                 410                 415

Tyr Arg Leu Ala Gly Asp Lys Val Gly Lys Leu Arg Val Phe Val Lys
            420                 425                 430

Asn Ser Asn Asn Ala Leu Ala Trp Glu Lys Thr Thr Ser Glu Asp Glu
        435                 440                 445

Lys Trp Lys Thr Gly Lys Ile Gln Leu Tyr Gln Gly Thr Asp Ala Thr
    450                 455                 460

Lys Ser Ile Ile Phe Glu Ala Glu Arg Gly Lys Gly Lys Thr Gly Glu
465                 470                 475                 480

Ile Ala Val Asp Gly Val Leu Val Ser Gly Leu Cys Pro Asp Ser
                485                 490                 495

Leu Leu Ser Val Asp Asp Xaa Met Val Leu Ser Leu Tyr Leu Thr Leu
            500                 505                 510

Tyr Val Ser Ser Leu Val Phe Leu Ile Leu His His Arg Thr Ser Gly
        515                 520                 525

Ile Leu Lys Leu Leu Ala Glu Lys Leu
    530                 535

<210> SEQ ID NO 5
<211> LENGTH: 2365
<212> TYPE: DNA
<213> ORGANISM: Homo sapiens
<220> FEATURE:
<221> NAME/KEY: CDS
<222> LOCATION: (205)...(1866)
<221> NAME/KEY: misc_feature
<222> LOCATION: (357)
<223> OTHER INFORMATION: Xaa = any amino acid

<400> SEQUENCE: 5
actagtgatt ccatcctaat acgactcact atagggctcg agcggccgcc c gggcaggtc    60
```

```
                                                              -continued tgcagggaca gcacccggta actgcgagtg gagcggagga cccgagcggc t gaggagaga       120 ggaggcggcg gcttagctgc tacggggtcc ggccggcgcc ctcccgaggg g ggctcagga       180 ggaggaagga ggaccgtgc gaga atg cct ctg ccc tgg agc ctt gcg ctc           231
                            Met Pro Leu Pro Trp Ser Leu Ala Leu
                              1               5 ccg ctg ctg ctc ccc tgg gtg gca ggt ggt t tc ggg aac gcg gcc agt        279
Pro Leu Leu Leu Pro Trp Val Ala Gly Gly P he Gly Asn Ala Ala Ser
 10              15                  20                  25 gca agg cat cac ggg ttg tta gca tcg gca c gt cag cct ggg gtc tgt        327
Ala Arg His His Gly Leu Leu Ala Ser Ala A rg Gln Pro Gly Val Cys
             30                  35                  40 cac tat gga act aaa ctg gcc tgc tgc tac g gc tgg aga aga aac agc        375
His Tyr Gly Thr Lys Leu Ala Cys Cys Tyr G ly Trp Arg Arg Asn Ser
         45                  50                  55 aag gga gtc tgt gaa gct aca tgc gaa cct g ga tgt aag ttt ggt gag        423
Lys Gly Val Cys Glu Ala Thr Cys Glu Pro G ly Cys Lys Phe Gly Glu
     60                  65                  70 tgc gtg gga cca aac aaa tgc aga tgc ttt c ca gga tac acc ggg aaa        471
Cys Val Gly Pro Asn Lys Cys Arg Cys Phe P ro Gly Tyr Thr Gly Lys
 75                  80                  85 acc tgc agt caa gat gtg aat gag tgt gga a tg aaa ccc cgg cca tgc        519
Thr Cys Ser Gln Asp Val Asn Glu Cys Gly M et Lys Pro Arg Pro Cys
 90                  95                 100                 105 caa cac aga tgt gtg aat aca cac gga agc t ac aag tgc ttt tgc ctc        567
Gln His Arg Cys Val Asn Thr His Gly Ser T yr Lys Cys Phe Cys Leu
             110                 115                 120 agt ggc cac atg ctc atg cca gat gct acg t gt gtg aac tct agg aca        615
Ser Gly His Met Leu Met Pro Asp Ala Thr C ys Val Asn Ser Arg Thr
         125                 130                 135 tgt gcc atg ata aac tgt cag tat agc tgt g aa gac aca gaa gaa ggg        663
Cys Ala Met Ile Asn Cys Gln Tyr Ser Cys G lu Asp Thr Glu Glu Gly
     140                 145                 150 cca cag tgc ctg tgt cca tcc tca gga ctc c gc ctg gcc cca aat gga        711
Pro Gln Cys Leu Cys Pro Ser Ser Gly Leu A rg Leu Ala Pro Asn Gly
 155                 160                 165 aga gac tgt cta gat att gat gaa tgt gcc t ct ggt aaa gtc atc tgt        759
Arg Asp Cys Leu Asp Ile Asp Glu Cys Ala S er Gly Lys Val Ile Cys
170                 175                 180                 185 ccc tac aat cga aga tgt gtg aac aca ttt g ga agc tac tac tgc aaa        807
Pro Tyr Asn Arg Arg Cys Val Asn Thr Phe G ly Ser Tyr Tyr Cys Lys
             190                 195                 200 tgt cac att ggt ttc gaa ctg caa tat atc a gt gga cga tat gac tgt        855
Cys His Ile Gly Phe Glu Leu Gln Tyr Ile S er Gly Arg Tyr Asp Cys
         205                 210                 215 ata gat ata aat gaa tgt act atg gat agc c at acg tgc agc cac cat        903
Ile Asp Ile Asn Glu Cys Thr Met Asp Ser H is Thr Cys Ser His His
     220                 225                 230 gcc aat tgc ttc aat acc caa ggg tcc ttc a ag tgt aaa tgc aag cag        951
Ala Asn Cys Phe Asn Thr Gln Gly Ser Phe L ys Cys Lys Cys Lys Gln
 235                 240                 245 gga tat aaa ggc aat gga ctt cgg tgt tct g ct atc cct gaa aat tct        999
Gly Tyr Lys Gly Asn Gly Leu Arg Cys Ser A la Ile Pro Glu Asn Ser
250                 255                 260                 265 gtg aag gaa gtc ctc aga gca cct ggt acc a tc aaa gac aga atc aag       1047
Val Lys Glu Val Leu Arg Ala Pro Gly Thr I le Lys Asp Arg Ile Lys
             270                 275                 280 aag ttg ctt gct cac aaa aac agc atg aaa a ag aag gca aaa att aaa       1095
Lys Leu Leu Ala His Lys Asn Ser Met Lys L ys Lys Ala Lys Ile Lys
         285                 290                 295
```

```
aat gtt acc cca gaa ccc acc agg act cct a cc cct aag gtg aac ttg    1143
Asn Val Thr Pro Glu Pro Thr Arg Thr Pro T hr Pro Lys Val Asn Leu
        300             305             310 cag ccc ttc aac tat gaa gag ata gtt tcc a ga ggc ggg aac tct cat    1191
Gln Pro Phe Asn Tyr Glu Glu Ile Val Ser A rg Gly Gly Asn Ser His
315             320             325 gga ggt aaa aaa ggg aat gaa gag aaa atg a aa gag ggg ctt gag gat    1239
Gly Gly Lys Lys Gly Asn Glu Glu Lys Met L ys Glu Gly Leu Glu Asp
330             335             340             345 gag aaa aga gaa gag aaa gcc ctg aag aat g ac wta gag gag cga agc    1287
Glu Lys Arg Glu Glu Lys Ala Leu Lys Asn A sp Xaa Glu Glu Arg Ser
        350             355             360 ctg cga gga gat gtg ttt ttc cct aag gtg a at gaa gca ggt gaa ttc    1335
Leu Arg Gly Asp Val Phe Phe Pro Lys Val A sn Glu Ala Gly Glu Phe
        365             370             375 ggc ctg att ctg gtc caa agg aaa gcg cta a ct tcc aaa ctg gaa cat    1383
Gly Leu Ile Leu Val Gln Arg Lys Ala Leu T hr Ser Lys Leu Glu His
        380             385             390 aaa gat tta aat atc tcg gtt gac tgc agc t tc aat cat ggg atc tgt    1431
Lys Asp Leu Asn Ile Ser Val Asp Cys Ser P he Asn His Gly Ile Cys
395             400             405 gac tgg aaa cag gat aga gaa gat gat ttt g ac tgg aat cct gct gat    1479
Asp Trp Lys Gln Asp Arg Glu Asp Asp Phe A sp Trp Asn Pro Ala Asp
410             415             420             425 cga gat aat gct att ggc ttc tat atg gca g tt ccg gcc ttg gca ggt    1527
Arg Asp Asn Ala Ile Gly Phe Tyr Met Ala V al Pro Ala Leu Ala Gly
        430             435             440 cac aag aaa gac att ggc cga ttg aaa ctt c tc cta cct gac ctg caa    1575
His Lys Lys Asp Ile Gly Arg Leu Lys Leu L eu Leu Pro Asp Leu Gln
        445             450             455 ccc caa agc aac ttc tgt ttg ctc ttt gat t ac cgg ctg gcc gga gac    1623
Pro Gln Ser Asn Phe Cys Leu Leu Phe Asp T yr Arg Leu Ala Gly Asp
        460             465             470 aaa gtc ggg aaa ctt cga gtg ttt gtg aaa a ac agt aac aat gcc ctg    1671
Lys Val Gly Lys Leu Arg Val Phe Val Lys A sn Ser Asn Asn Ala Leu
        475             480             485 gca tgg gag aag acc acg agt gag gat gaa a ag tgg aag aca ggg aaa    1719
Ala Trp Glu Lys Thr Thr Ser Glu Asp Glu L ys Trp Lys Thr Gly Lys
490             495             500             505 att cag ttg tat caa gga act gat gct acc a aa agc atc att ttt gaa    1767
Ile Gln Leu Tyr Gln Gly Thr Asp Ala Thr L ys Ser Ile Ile Phe Glu
        510             515             520 gca gaa cgt ggc aag ggc aaa acc ggc gaa a tc gca gtg gat ggc gtc    1815
Ala Glu Arg Gly Lys Gly Lys Thr Gly Glu I le Ala Val Asp Gly Val
        525             530             535 ttg ctt gtt tca ggc tta tgt cca gat agc c tt tta tct gtg gat gac    1863
Leu Leu Val Ser Gly Leu Cys Pro Asp Ser L eu Leu Ser Val Asp Asp
        540             545             550 tga atgttactat ctttatattt gactttgtat gtcagttccc tggttttt tt         1916
  * gatattgsat cataggacct ctggcatttt aaaattacta agctgaaaaa t tgtaatgta    1976 ccaacagaaa ttattattgt aagatgcctt tmttgtataa gatatgccaa t atttgcttt    2036 aaatatcata tcactgtatc ttctcagtca tttctgaatc tttccacatt a tattataaa    2096 atatggaaat gtcaggttta tctcccctcc tcagtatatc tgatttgtat a agtaagttg    2156 atgagcttct ctctgcaaca tttctagaaa atagahaaaa aagcacagag a aatgtttaa    2216 ctgtttgact cttatgatag tttttggaaa ctatgacatc aaagatagac t tttgcctaa    2276
```

```
gtggcttagc tgggtctttc atagccaaac ttgtatattt aaattctttg t aataataat    2336 atccaaatca tcaaaaaaaa aaaaaaaaa                                        2365
```

<210> SEQ ID NO 6
<211> LENGTH: 553
<212> TYPE: PRT
<213> ORGANISM: Homo sapiens
<220> FEATURE:
<221> NAME/KEY: misc_feature
<222> LOCATION: (357)
<223> OTHER INFORMATION: Xaa = any amino acid

<400> SEQUENCE: 6

```
Met Pro Leu Pro Trp Ser Leu Ala Leu Pro L eu Leu Leu Pro Trp Val
 1               5                  10                   15

Ala Gly Gly Phe Gly Asn Ala Ala Ser Ala A rg His His Gly Leu Leu
                20                  25                   30

Ala Ser Ala Arg Gln Pro Gly Val Cys His T yr Gly Thr Lys Leu Ala
            35                  40                   45

Cys Cys Tyr Gly Trp Arg Arg Asn Ser Lys G ly Val Cys Glu Ala Thr
50                  55                  60

Cys Glu Pro Gly Cys Lys Phe Gly Glu Cys V al Gly Pro Asn Lys Cys
65                  70                  75                   80

Arg Cys Phe Pro Gly Tyr Thr Gly Lys Thr C ys Ser Gln Asp Val Asn
                85                  90                   95

Glu Cys Gly Met Lys Pro Arg Pro Cys Gln H is Arg Cys Val Asn Thr
            100                 105                  110

His Gly Ser Tyr Lys Cys Phe Cys Leu Ser G ly His Met Leu Met Pro
        115                 120                  125

Asp Ala Thr Cys Val Asn Ser Arg Thr Cys A la Met Ile Asn Cys Gln
    130                 135                  140

Tyr Ser Cys Glu Asp Thr Glu Glu Gly Pro G ln Cys Leu Cys Pro Ser
145                 150                 155                  160

Ser Gly Leu Arg Leu Ala Pro Asn Gly Arg A sp Cys Leu Asp Ile Asp
                165                 170                  175

Glu Cys Ala Ser Gly Lys Val Ile Cys Pro T yr Asn Arg Arg Cys Val
            180                 185                  190

Asn Thr Phe Gly Ser Tyr Tyr Cys Lys Cys H is Ile Gly Phe Glu Leu
        195                 200                  205

Gln Tyr Ile Ser Gly Arg Tyr Asp Cys Ile A sp Ile Asn Glu Cys Thr
    210                 215                  220

Met Asp Ser His Thr Cys Ser His Ala A sn Cys Phe Asn Thr Gln
225                 230                 235                  240

Gly Ser Phe Lys Cys Lys Cys Lys Gln Gly T yr Lys Gly Asn Gly Leu
                245                 250                  255

Arg Cys Ser Ala Ile Pro Glu Asn Ser Val L ys Glu Val Leu Arg Ala
            260                 265                  270

Pro Gly Thr Ile Lys Asp Arg Ile Lys Lys L eu Leu Ala His Lys Asn
        275                 280                  285

Ser Met Lys Lys Lys Ala Lys Ile Lys Asn V al Thr Pro Glu Pro Thr
    290                 295                  300

Arg Thr Pro Thr Pro Lys Val Asn Leu Gln P ro Phe Asn Tyr Glu Glu
305                 310                 315                  320

Ile Val Ser Arg Gly Gly Asn Ser His Gly G ly Lys Lys Gly Asn Glu
                325                 330                  335
```

```
Glu Lys Met Lys Glu Gly Leu Glu Asp Glu Lys Arg Glu Glu Lys Ala
                340                 345                 350

Leu Lys Asn Asp Xaa Glu Glu Arg Ser Leu Arg Gly Asp Val Phe Phe
            355                 360                 365

Pro Lys Val Asn Glu Ala Gly Glu Phe Gly Leu Ile Leu Val Gln Arg
        370                 375                 380

Lys Ala Leu Thr Ser Lys Leu Glu His Lys Asp Leu Asn Ile Ser Val
385                 390                 395                 400

Asp Cys Ser Phe Asn His Gly Ile Cys Asp Trp Lys Gln Asp Arg Glu
                405                 410                 415

Asp Asp Phe Asp Trp Asn Pro Ala Asp Arg Asp Asn Ala Ile Gly Phe
            420                 425                 430

Tyr Met Ala Val Pro Ala Leu Ala Gly His Lys Lys Asp Ile Gly Arg
        435                 440                 445

Leu Lys Leu Leu Leu Pro Asp Leu Gln Pro Gln Ser Asn Phe Cys Leu
    450                 455                 460

Leu Phe Asp Tyr Arg Leu Ala Gly Asp Lys Val Gly Lys Leu Arg Val
465                 470                 475                 480

Phe Val Lys Asn Ser Asn Asn Ala Leu Ala Trp Glu Lys Thr Thr Ser
                485                 490                 495

Glu Asp Glu Lys Trp Lys Thr Gly Lys Ile Gln Leu Tyr Gln Gly Thr
            500                 505                 510

Asp Ala Thr Lys Ser Ile Ile Phe Glu Ala Glu Arg Gly Lys Gly Lys
        515                 520                 525

Thr Gly Glu Ile Ala Val Asp Gly Val Leu Val Ser Gly Leu Cys
    530                 535                 540

Pro Asp Ser Leu Leu Ser Val Asp Asp
545                 550

<210> SEQ ID NO 7
<211> LENGTH: 42
<212> TYPE: PRT
<213> ORGANISM: Drosophila Melanogaster
<220> FEATURE:
<221> NAME/KEY: misc_feature
<222> LOCATION: (5)
<223> OTHER INFORMATION: Xaa = any amino acid
<221> NAME/KEY: misc_feature
<222> LOCATION: (16-18)
<223> OTHER INFORMATION: Xaa = any amino acid
<221> NAME/KEY: misc_feature
<222> LOCATION: (20)
<223> OTHER INFORMATION: Xaa = any amino acid
<221> NAME/KEY: misc_feature
<222> LOCATION: (25)
<223> OTHER INFORMATION: Xaa = any amino acid
<221> NAME/KEY: misc_feature
<222> LOCATION: (27)
<223> OTHER INFORMATION: Xaa = any amino acid
<221> NAME/KEY: misc_feature
<222> LOCATION: (36-38)
<223> OTHER INFORMATION: Xaa = any amino acid
<221> NAME/KEY: misc_feature
<222> LOCATION: (41)
<223> OTHER INFORMATION: Xaa = any amino acid

<400> SEQUENCE: 7

Ile Asp Glu Cys Xaa Ser Asn Pro Cys Gln Asn Gly Gly Thr Cys Xaa
1               5                   10                  15

Xaa Xaa Asp Xaa Val Gly Ser Tyr Xaa Cys Xaa Cys Pro Pro Gly Phe
            20                  25                  30
```

```
Thr Gly Lys Xaa Xaa Xaa Cys Glu Xaa Asn
         35                  40
```

<210> SEQ ID NO 8
<211> LENGTH: 39
<212> TYPE: PRT
<213> ORGANISM: Homo sapiens
<220> FEATURE:
<221> NAME/KEY: misc_feature
<222> LOCATION: (1)
<223> OTHER INFORMATION: Xaa = any amino acid
<221> NAME/KEY: misc_feature
<222> LOCATION: (7-9)
<223> OTHER INFORMATION: Xaa = any amino acid
<221> NAME/KEY: misc_feature
<222> LOCATION: (13-15)
<223> OTHER INFORMATION: Xaa = any amino acid
<221> NAME/KEY: misc_feature
<222> LOCATION: (20)
<223> OTHER INFORMATION: Xaa = any amino acid
<221> NAME/KEY: misc_feature
<222> LOCATION: (24)
<223> OTHER INFORMATION: Xaa = any amino acid
<221> NAME/KEY: misc_feature
<222> LOCATION: (28)
<223> OTHER INFORMATION: Xaa = any amino acid
<221> NAME/KEY: misc_feature
<222> LOCATION: (31-32)
<223> OTHER INFORMATION: Xaa = any amino acid
<221> NAME/KEY: misc_feature
<222> LOCATION: (34-35)
<223> OTHER INFORMATION: Xaa = any amino acid
<221> NAME/KEY: misc_feature
<222> LOCATION: (37)
<223> OTHER INFORMATION: Xaa = any amino acid

<400> SEQUENCE: 8

```
Xaa Asn Glu Cys Thr Met Xaa Xaa Xaa Cys Gln His Xaa Xaa Xaa Cys
 1               5                  10                  15

Val Asn Thr Xaa Gly Ser Tyr Xaa Cys Lys Cys Xaa Ser Gly Xaa Xaa
             20                  25                  30

Gly Xaa Xaa Leu Xaa Cys Asp
         35
```

<210> SEQ ID NO 9
<211> LENGTH: 164
<212> TYPE: PRT
<213> ORGANISM: Homo sapiens

<400> SEQUENCE: 9

```
Cys Arg Cys Phe Pro Gly Tyr Thr Gly Lys Thr Cys Ser Gln Val Asn
 1               5                  10                  15

Glu Cys Gly Met Lys Pro Arg Pro Cys Gln His Arg Cys Val Asn Thr
             20                  25                  30

His Gly Ser Tyr Lys Cys Phe Cys Leu Ser Gly His Met Leu Met Pro
         35                  40                  45

Asp Val Asn Ser Arg Thr Cys Ala Met Ile Asn Cys Gln Tyr Ser Cys
     50                  55                  60

Glu Asp Thr Glu Glu Gly Pro Gln Cys Leu Cys Pro Ser Ser Gly Leu
 65                  70                  75                  80

Arg Leu Ala Pro Asn Ile Asp Glu Cys Ala Ser Gly Lys Val Ile Cys
                 85                  90                  95

Pro Tyr Asn Arg Arg Cys Val Asn Thr Phe Gly Ser Tyr Tyr Cys Lys
             100                 105                 110

Cys His Ile Gly Phe Glu Leu Gln Tyr Ile Ser Gly Arg Ile Asn Glu
         115                 120                 125
```

Cys Thr Met Asp Ser His Thr Cys Ser His His Ala Asn Cys Phe Asn
            130                 135                 140

Thr Gln Gly Ser Phe Cys Lys Cys Lys Gln Gly Tyr Lys Gly Asn Gly
145                 150                 155                 160

Leu Arg Cys Ser

<210> SEQ ID NO 10
<211> LENGTH: 45
<212> TYPE: PRT
<213> ORGANISM: Homo sapiens
<220> FEATURE:
<221> NAME/KEY: misc_feature
<222> LOCATION: (2)
<223> OTHER INFORMATION: Xaa = any amino acid
<221> NAME/KEY: misc_feature
<222> LOCATION: (5)
<223> OTHER INFORMATION: Xaa = any amino acid
<221> NAME/KEY: misc_feature
<222> LOCATION: (10-11)
<223> OTHER INFORMATION: Xaa = any amino acid
<221> NAME/KEY: misc_feature
<222> LOCATION: (13)
<223> OTHER INFORMATION: Xaa = any amino acid
<221> NAME/KEY: misc_feature
<222> LOCATION: (16-17)
<223> OTHER INFORMATION: Xaa = any amino acid
<221> NAME/KEY: misc_feature
<222> LOCATION: (19)
<223> OTHER INFORMATION: Xaa = any amino acid
<221> NAME/KEY: misc_feature
<222> LOCATION: (26)
<223> OTHER INFORMATION: Xaa = any amino acid
<221> NAME/KEY: misc_feature
<222> LOCATION: (34)
<223> OTHER INFORMATION: Xaa = any amino acid
<221> NAME/KEY: misc_feature
<222> LOCATION: (36)
<223> OTHER INFORMATION: Xaa = any amino acid
<221> NAME/KEY: misc_feature
<222> LOCATION: (39)
<223> OTHER INFORMATION: Xaa = any amino acid
<221> NAME/KEY: misc_feature
<222> LOCATION: (42-44)
<223> OTHER INFORMATION: Xaa = any amino acid

<400> SEQUENCE: 10

Val Xaa Glu Cys Xaa Ser Gly Xaa Gln Xaa Xaa Cys Xaa Ser Ser Xaa
1               5                   10                  15

Xaa Cys Xaa Asn Thr Val Gly Ser Tyr Xaa Cys Arg Cys Arg Pro Gly
            20                  25                  30

Trp Xaa Pro Xaa Pro Gly Xaa Pro Asn Xaa Xaa Xaa Asp
        35                  40                  45

<210> SEQ ID NO 11
<211> LENGTH: 58
<212> TYPE: PRT
<213> ORGANISM: Mammalian
<220> FEATURE:
<221> NAME/KEY: misc_feature
<222> LOCATION: (39-41)
<223> OTHER INFORMATION: Xaa = any amino acid
<221> NAME/KEY: misc_feature
<222> LOCATION: (45-46)
<223> OTHER INFORMATION: Xaa = any amino acid

<400> SEQUENCE: 11

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn

```
                    20                  25                  30
Cys Val Val Gly Tyr Ile Xaa Xaa Xaa Gly Glu Arg Xaa Xaa Cys Gln
                35                  40                  45

Tyr Arg Asp Leu Lys Trp Trp Glu Leu Arg
     50                  55
```

<210> SEQ ID NO 12
<211> LENGTH: 21
<212> TYPE: DNA
<213> ORGANISM: Artificial Sequence
<220> FEATURE:
<223> OTHER INFORMATION: Gene-specific PCR primer 10244-52

<400> SEQUENCE: 12
ctcatcctca agcccctctt t                                           21

<210> SEQ ID NO 13
<211> LENGTH: 21
<212> TYPE: DNA
<213> ORGANISM: Artificial Sequence
<220> FEATURE:
<223> OTHER INFORMATION: Gene-specific PCR primer 10244-51

<400> SEQUENCE: 13
ccatgagagt tcccgcctct g                                           21

<210> SEQ ID NO 14
<211> LENGTH: 21
<212> TYPE: DNA
<213> ORGANISM: Artificial Sequence
<220> FEATURE:
<223> OTHER INFORMATION: Vector primer T7

<400> SEQUENCE: 14
gtaatacgac tcactatagg g                                           21

<210> SEQ ID NO 15
<211> LENGTH: 22
<212> TYPE: DNA
<213> ORGANISM: Artificial Sequence
<220> FEATURE:
<223> OTHER INFORMATION: Vector primer SP6

<400> SEQUENCE: 15
atttaggtga cactatagaa gg                                          22

<210> SEQ ID NO 16
<211> LENGTH: 21
<212> TYPE: DNA
<213> ORGANISM: Artificial Sequence
<220> FEATURE:
<223> OTHER INFORMATION: Gene-specific PCR primer 10244-A

<400> SEQUENCE: 16
cccaggctga cgtgccgatg c                                           21

<210> SEQ ID NO 17
<211> LENGTH: 21
<212> TYPE: DNA
<213> ORGANISM: Artificial Sequence
<220> FEATURE:
<223> OTHER INFORMATION: Gene-specific PCR primer 10244-B

<400> SEQUENCE: 17
gcagcaggcc agtttagttc c                                           21

```
<210> SEQ ID NO 18
<211> LENGTH: 502
<212> TYPE: PRT
<213> ORGANISM: Homo sapiens
<220> FEATURE:
<221> NAME/KEY: misc_feature
<222> LOCATION: (501-502)
<223> OTHER INFORMATION: Xaa = any amino acid

<400> SEQUENCE: 18
```

Gly Trp Arg Arg Asn Ser Lys Gly Val Cys Glu Ala Thr Cys Glu Pro
 1               5                  10                  15

Gly Cys Lys Phe Gly Glu Cys Val Gly Pro Asn Lys Cys Arg Cys Phe
            20                  25                  30

Pro Gly Tyr Thr Gly Lys Thr Cys Ser Gln Asp Val Asn Glu Cys Gly
        35                  40                  45

Met Lys Pro Arg Pro Cys Gln His Arg Cys Val Asn Thr His Gly Ser
50                  55                  60

Tyr Lys Cys Phe Cys Leu Ser Gly His Met Leu Met Pro Asp Ala Thr
65                  70                  75                  80

Cys Val Asn Ser Arg Thr Cys Ala Met Ile Asn Cys Gln Tyr Ser Cys
                85                  90                  95

Glu Asp Thr Glu Glu Gly Pro Gln Cys Leu Cys Pro Ser Ser Gly Leu
            100                 105                 110

Arg Leu Ala Pro Asn Gly Arg Asp Cys Leu Asp Ile Asp Glu Cys Ala
        115                 120                 125

Ser Gly Lys Val Ile Cys Pro Tyr Asn Arg Arg Cys Val Asn Thr Phe
130                 135                 140

Gly Ser Tyr Tyr Cys Lys Cys His Ile Gly Phe Glu Leu Gln Tyr Ile
145                 150                 155                 160

Ser Gly Arg Tyr Asp Cys Ile Asp Ile Asn Glu Cys Thr Met Asp Ser
                165                 170                 175

His Thr Cys Ser His His Ala Asn Cys Phe Asn Thr Gln Gly Ser Phe
            180                 185                 190

Lys Cys Lys Cys Lys Gln Gly Tyr Lys Gly Asn Gly Leu Arg Cys Ser
        195                 200                 205

Ala Ile Pro Glu Asn Ser Val Lys Glu Val Leu Arg Ala Pro Gly Thr
210                 215                 220

Ile Lys Asp Arg Ile Lys Lys Leu Leu Ala His Lys Asn Ser Met Lys
225                 230                 235                 240

Lys Lys Ala Lys Ile Lys Asn Val Thr Pro Glu Pro Thr Arg Thr Pro
                245                 250                 255

Thr Pro Lys Val Asn Leu Gln Pro Phe Asn Tyr Glu Glu Ile Val Ser
            260                 265                 270

Arg Gly Gly Asn Ser His Gly Lys Lys Gly Asn Glu Glu Lys Met
        275                 280                 285

Lys Glu Gly Leu Glu Asp Glu Lys Arg Glu Glu Lys Ala Leu Lys Asn
290                 295                 300

Asp Ile Glu Glu Arg Ser Leu Arg Gly Asp Val Phe Phe Pro Lys Val
305                 310                 315                 320

Asn Glu Ala Gly Glu Phe Gly Leu Ile Leu Val Gln Arg Lys Ala Leu
                325                 330                 335

Thr Ser Lys Leu Glu His Lys Asp Leu Asn Ile Ser Val Asp Cys Ser
            340                 345                 350

```
Phe Asn His Gly Ile Cys Asp Trp Lys Gln Asp Arg Glu Asp Asp Phe
            355                 360                 365

Asp Trp Asn Pro Ala Asp Arg Asp Asn Ala Ile Gly Phe Tyr Met Ala
        370                 375                 380

Val Pro Ala Leu Ala Gly His Met Lys Asp Ile Gly Arg Leu Lys Leu
385                 390                 395                 400

Leu Leu Pro Asp Leu Gln Pro Gln Ser Asn Phe Cys Leu Leu Phe Asp
                405                 410                 415

Tyr Arg Leu Ala Gly Asp Lys Val Gly Lys Leu Arg Val Phe Val Lys
            420                 425                 430

Asn Ser Asn Asn Ala Leu Ala Trp Glu Lys Thr Thr Ser Glu Asp Glu
        435                 440                 445

Lys Trp Lys Thr Gly Lys Ile Gln Leu Tyr Gln Gly Thr Asp Ala Thr
    450                 455                 460

Lys Ser Ile Ile Phe Glu Ala Glu Arg Gly Lys Gly Lys Thr Gly Glu
465                 470                 475                 480

Ile Ala Val Asp Gly Val Leu Leu Val Ser Gly Leu Cys Pro Asp Ser
                485                 490                 495

Leu Leu Ser Val Xaa Xaa
            500

<210> SEQ ID NO 19
<211> LENGTH: 21
<212> TYPE: DNA
<213> ORGANISM: Artificial Sequence
<220> FEATURE:
<223> OTHER INFORMATION: Description of Artificial  Sequence: primer

<400> SEQUENCE: 19
gtcatttctg aatctttcca c                                          21

<210> SEQ ID NO 20
<211> LENGTH: 22
<212> TYPE: DNA
<213> ORGANISM: Artificial Sequence
<220> FEATURE:
<223> OTHER INFORMATION: Description of Artificial  Sequence: primer

<400> SEQUENCE: 20
gaaatgttgc agagagaagc tc                                         22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial  Sequence: primer

<400> SEQUENCE: 21
ccagaaccca ccaggactcc                                            20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial  Sequence: primer

<400> SEQUENCE: 22
gggaactgac atacaaagtc                                            20
```

```
<210> SEQ ID NO 23
<211> LENGTH: 2365
<212> TYPE: DNA
<213> ORGANISM: Homo sapiens
<220> FEATURE:
<221> NAME/KEY: CDS
<222> LOCATION: (205)..(1863)

<400> SEQUENCE: 23
actagtgatt ccatcctaat acgactcact atagggctcg agcggccgcc c gggcaggtc      60 tgcagggaca gcacccggta actgcgagtg gagcggagga cccgagcggc t gaggagaga    120 ggaggcggcg gcttagctgc tacggggtcc ggccggcgcc ctcccgaggg g ggctcagga    180 ggaggaagga ggaccgtgc gaga atg cct ctg ccc tgg agc ctt gcg ctc         231
                           Met Pro Leu Pro Trp Ser Leu Ala Leu
                             1               5 ccg ctg ctg ctc tcc tgg gtg gca ggt ggt t tc ggg aac gcg gcc agt      279
Pro Leu Leu Leu Ser Trp Val Ala Gly Gly P he Gly Asn Ala Ala Ser
 10              15                  20                  25 gca agg cat cac ggg ttg tta gca tcg gca c gt cag cct ggg gtc tgt      327
Ala Arg His His Gly Leu Leu Ala Ser Ala A rg Gln Pro Gly Val Cys
             30                  35                  40 cac tat gga act aaa ctg gcc tgc tgc tac g gc tgg aga aga aac agc      375
His Tyr Gly Thr Lys Leu Ala Cys Cys Tyr G ly Trp Arg Arg Asn Ser
         45                  50                  55 aag gga gtc tgt gaa gct aca tgc gaa cct g ga tgt aag ttt ggt gag      423
Lys Gly Val Cys Glu Ala Thr Cys Glu Pro G ly Cys Lys Phe Gly Glu
     60                  65                  70 tgc gtg gga cca aac aaa tgc aga tgc ttt c ca gga tac acc ggg aaa      471
Cys Val Gly Pro Asn Lys Cys Arg Cys Phe P ro Gly Tyr Thr Gly Lys
 75                  80                  85 acc tgc agt caa gat gtg aat gag tgt gga a tg aaa ccc cgg cca tgc      519
Thr Cys Ser Gln Asp Val Asn Glu Cys Gly M et Lys Pro Arg Pro Cys
             90                  95                 100                 105 caa cac aga tgt gtg aat aca cac gga agc t ac aag tgc ttt tgc ctc      567
Gln His Arg Cys Val Asn Thr His Gly Ser T yr Lys Cys Phe Cys Leu
                110                 115                 120 agt ggc cac atg ctc atg cca gat gct acg t gt gtg aac tct agg aca      615
Ser Gly His Met Leu Met Pro Asp Ala Thr C ys Val Asn Ser Arg Thr
            125                 130                 135 tgt gcc atg ata aac tgt cag tat agc tgt g aa gac aca gaa gaa ggg      663
Cys Ala Met Ile Asn Cys Gln Tyr Ser Cys G lu Asp Thr Glu Glu Gly
        140                 145                 150 cca cag tgc ctg tgt cca tcc tca gga ctc c gc ctg gcc cca aat gga      711
Pro Gln Cys Leu Cys Pro Ser Ser Gly Leu A rg Leu Ala Pro Asn Gly
    155                 160                 165 aga gac tgt cta gat att gat gaa tgt gcc t ct ggt aaa gtc atc tgt      759
Arg Asp Cys Leu Asp Ile Asp Glu Cys Ala S er Gly Lys Val Ile Cys
170                 175                 180                 185 ccc tac aat cga aga tgt gtg aac aca ttt g ga agc tac tac tgc aaa      807
Pro Tyr Asn Arg Arg Cys Val Asn Thr Phe G ly Ser Tyr Tyr Cys Lys
                190                 195                 200 tgt cac att ggt ttc gaa ctg caa tat atc a gt gga cga tat gac tgt      855
Cys His Ile Gly Phe Glu Leu Gln Tyr Ile S er Gly Arg Tyr Asp Cys
            205                 210                 215 ata gat ata aat gaa tgt act atg gat agc c at acg tgc agc cac cat      903
Ile Asp Ile Asn Glu Cys Thr Met Asp Ser H is Thr Cys Ser His His
        220                 225                 230 gcc aat tgc ttc aat acc caa ggg tcc ttc a ag tgt aaa tgc aag cag      951
Ala Asn Cys Phe Asn Thr Gln Gly Ser Phe L ys Cys Lys Cys Lys Gln
    235                 240                 245
```

```
gga tat aaa ggc aat gga ctt cgg tgt tct g ct atc cct gaa aat tct    999
Gly Tyr Lys Gly Asn Gly Leu Arg Cys Ser A la Ile Pro Glu Asn Ser
250             255                 260              265 gtg aag gaa gtc ctc aga gca cct ggt acc a tc aaa gac aga atc aag   1047
Val Lys Glu Val Leu Arg Ala Pro Gly Thr I le Lys Asp Arg Ile Lys
            270                 275                  280 aag ttg ctt gct cac aaa aac agc atg aaa a ag aag gca aaa att aaa   1095
Lys Leu Leu Ala His Lys Asn Ser Met Lys L ys Lys Ala Lys Ile Lys
                285                 290                  295 aat gtt acc cca gaa ccc acc agg act cct a cc cct aag gtg aac ttg   1143
Asn Val Thr Pro Glu Pro Thr Arg Thr Pro T hr Pro Lys Val Asn Leu
            300                 305                  310 cag ccc ttc aac tat gaa gag ata gtt tcc a ga ggc ggg aac tct cat   1191
Gln Pro Phe Asn Tyr Glu Glu Ile Val Ser A rg Gly Gly Asn Ser His
        315                 320                  325 gga ggt aaa aaa ggg aat gaa gag aaa atg a aa gag ggg ctt gag gat   1239
Gly Gly Lys Lys Gly Asn Glu Glu Lys Met L ys Glu Gly Leu Glu Asp
330             335                 340                  345 gag aaa aga gaa gag aaa gcc ctg aag aat g ac ata gag gag cga agc   1287
Glu Lys Arg Glu Glu Lys Ala Leu Lys Asn A sp Ile Glu Glu Arg Ser
                350                 355                  360 ctg cga gga gat gtg ttt ttc cct aag gtg a at gaa gca ggt gaa ttc   1335
Leu Arg Gly Asp Val Phe Phe Pro Lys Val A sn Glu Ala Gly Glu Phe
            365                 370                  375 ggc ctg att ctg gtc caa agg aaa gcg cta a ct tcc aaa ctg gaa cat   1383
Gly Leu Ile Leu Val Gln Arg Lys Ala Leu T hr Ser Lys Leu Glu His
        380                 385                  390 aaa gat tta aat atc tcg gtt gac tgc agc t tc aat cat ggg atc tgt   1431
Lys Asp Leu Asn Ile Ser Val Asp Cys Ser P he Asn His Gly Ile Cys
    395                 400                  405 gac tgg aaa cag gat aga gaa gat gat ttt g ac tgg aat cct gct gat   1479
Asp Trp Lys Gln Asp Arg Glu Asp Asp Phe A sp Trp Asn Pro Ala Asp
410             415                 420                  425 cga gat aat gct att ggc ttc tat atg gca g tt ccg gcc ttg gca ggt   1527
Arg Asp Asn Ala Ile Gly Phe Tyr Met Ala V al Pro Ala Leu Ala Gly
                430                 435                  440 cac aag aaa gac att ggc cga ttg aaa ctt c tc cta cct gac ctg caa   1575
His Lys Lys Asp Ile Gly Arg Leu Lys Leu L eu Leu Pro Asp Leu Gln
            445                 450                  455 ccc caa agc aac ttc tgt ttg ctc ttt gat t ac cgg ctg gcc gga gac   1623
Pro Gln Ser Asn Phe Cys Leu Leu Phe Asp T yr Arg Leu Ala Gly Asp
        460                 465                  470 aaa gtc ggg aaa ctt cga gtg ttt gtg aaa a ac agt aac aat gcc ctg   1671
Lys Val Gly Lys Leu Arg Val Phe Val Lys A sn Ser Asn Asn Ala Leu
    475                 480                  485 gca tgg gag aag acc acg agt gag gat gaa a ag tgg aag aca ggg aaa   1719
Ala Trp Glu Lys Thr Thr Ser Glu Asp Glu L ys Trp Lys Thr Gly Lys
490             495                 500                  505 att cag ttg tat caa gga act gat gct acc a aa agc atc att ttt gaa   1767
Ile Gln Leu Tyr Gln Gly Thr Asp Ala Thr L ys Ser Ile Ile Phe Glu
                510                 515                  520 gca gaa cgt ggc aag ggc aaa acc ggc gaa a tc gca gtg gat ggc gtc   1815
Ala Glu Arg Gly Lys Gly Lys Thr Gly Glu I le Ala Val Asp Gly Val
            525                 530                  535 ttg ctt gtt tca ggc tta tgt cca gat agc c tt tta tct gtg gat gac   1863
Leu Leu Val Ser Gly Leu Cys Pro Asp Ser L eu Leu Ser Val Asp Asp
        540                 545                  550 tgaatgttac tatctttata tttgactttg tatgtcagtt ccctggtttt t ttgatattg   1923
```

```
satcatagga cctctggcat tttaaaatta ctaagctgaa aaattgtaat g taccaacag    1983 aaattattat tgtaagatgc ctttmttgta taagatatgc caatatttgc t ttaaatatc    2043 atatcactgt atcttctcag tcatttctga atctttccac attatattat a aaatatgga    2103 aatgtcaggt ttatctcccc tcctcagtat atctgatttg tataagtaag t tgatgagct    2163 tctctctgca acatttctag aaaatagaha aaaaagcaca gagaaatgtt t aactgtttg    2223 actcttatga tagttttttgg aaactatgac atcaaagata gacttttgcc t aagtggctt    2283 agctgggtct tcatagcca aacttgtata tttaaattct tgtaataat a atatccaaa    2343 tcatcaaaaa aaaaaaaaaa aa                                            2365
```

<210> SEQ ID NO 24
<211> LENGTH: 553
<212> TYPE: PRT
<213> ORGANISM: Homo sapiens

<400> SEQUENCE: 24

```
Met Pro Leu Pro Trp Ser Leu Ala Leu Pro Leu Leu Ser Trp Val
 1               5                  10                  15

Ala Gly Gly Phe Gly Asn Ala Ala Ser Ala Arg His His Gly Leu Leu
            20                  25                  30

Ala Ser Ala Arg Gln Pro Gly Val Cys His Tyr Gly Thr Lys Leu Ala
        35                  40                  45

Cys Cys Tyr Gly Trp Arg Arg Asn Ser Lys Gly Val Cys Glu Ala Thr
    50                  55                  60

Cys Glu Pro Gly Cys Lys Phe Gly Glu Cys Val Gly Pro Asn Lys Cys
65                  70                  75                  80

Arg Cys Phe Pro Gly Tyr Thr Gly Lys Thr Cys Ser Gln Asp Val Asn
                85                  90                  95

Glu Cys Gly Met Lys Pro Arg Pro Cys Gln His Arg Cys Val Asn Thr
            100                 105                 110

His Gly Ser Tyr Lys Cys Phe Cys Leu Ser Gly His Met Leu Met Pro
        115                 120                 125

Asp Ala Thr Cys Val Asn Ser Arg Thr Cys Ala Met Ile Asn Cys Gln
    130                 135                 140

Tyr Ser Cys Glu Asp Thr Glu Glu Gly Pro Gln Cys Leu Cys Pro Ser
145                 150                 155                 160

Ser Gly Leu Arg Leu Ala Pro Asn Gly Arg Asp Cys Leu Asp Ile Asp
                165                 170                 175

Glu Cys Ala Ser Gly Lys Val Ile Cys Pro Tyr Asn Arg Arg Cys Val
            180                 185                 190

Asn Thr Phe Gly Ser Tyr Tyr Cys Lys Cys His Ile Gly Phe Glu Leu
        195                 200                 205

Gln Tyr Ile Ser Gly Arg Tyr Asp Cys Ile Asp Ile Asn Glu Cys Thr
    210                 215                 220

Met Asp Ser His Thr Cys Ser His Ala Asn Cys Phe Asn Thr Gln
225                 230                 235                 240

Gly Ser Phe Lys Cys Lys Cys Lys Gln Gly Tyr Lys Gly Asn Gly Leu
                245                 250                 255

Arg Cys Ser Ala Ile Pro Glu Asn Ser Val Lys Glu Val Leu Arg Ala
            260                 265                 270

Pro Gly Thr Ile Lys Asp Arg Ile Lys Lys Leu Leu Ala His Lys Asn
        275                 280                 285
```

-continued

```
Ser Met Lys Lys Lys Ala Lys Ile Lys Asn Val Thr Pro Glu Pro Thr
    290                 295                 300

Arg Thr Pro Thr Pro Lys Val Asn Leu Gln Pro Phe Asn Tyr Glu Glu
305                 310                 315                 320

Ile Val Ser Arg Gly Gly Asn Ser His Gly Gly Lys Lys Gly Asn Glu
                325                 330                 335

Glu Lys Met Lys Glu Gly Leu Glu Asp Glu Lys Arg Glu Glu Lys Ala
            340                 345                 350

Leu Lys Asn Asp Ile Glu Glu Arg Ser Leu Arg Gly Asp Val Phe Phe
                355                 360                 365

Pro Lys Val Asn Glu Ala Gly Glu Phe Gly Leu Ile Leu Val Gln Arg
        370                 375                 380

Lys Ala Leu Thr Ser Lys Leu Glu His Lys Asp Leu Asn Ile Ser Val
385                 390                 395                 400

Asp Cys Ser Phe Asn His Gly Ile Cys Asp Trp Lys Gln Asp Arg Glu
                405                 410                 415

Asp Asp Phe Asp Trp Asn Pro Ala Asp Arg Asp Asn Ala Ile Gly Phe
                420                 425                 430

Tyr Met Ala Val Pro Ala Leu Ala Gly His Lys Lys Asp Ile Gly Arg
            435                 440                 445

Leu Lys Leu Leu Leu Pro Asp Leu Gln Pro Gln Ser Asn Phe Cys Leu
        450                 455                 460

Leu Phe Asp Tyr Arg Leu Ala Gly Asp Lys Val Gly Lys Leu Arg Val
465                 470                 475                 480

Phe Val Lys Asn Ser Asn Asn Ala Leu Ala Trp Glu Lys Thr Thr Ser
                485                 490                 495

Glu Asp Glu Lys Trp Lys Thr Gly Lys Ile Gln Leu Tyr Gln Gly Thr
            500                 505                 510

Asp Ala Thr Lys Ser Ile Ile Phe Glu Ala Glu Arg Gly Lys Gly Lys
            515                 520                 525

Thr Gly Glu Ile Ala Val Asp Gly Val Leu Val Ser Gly Leu Cys
        530                 535                 540

Pro Asp Ser Leu Leu Ser Val Asp Asp
545                 550
```

ANTIBODIES SPECIFIC FOR EGF MOTIF PROTEINS

1. RELATED APPLICATIONS

This patent application is a continuation-in-part of U.S. patent application Ser. No. 09/249,697 filed Feb. 12, 1999, which is a continuation-in-part of U.S. patent application Ser. No. 08/968,800 filed Nov. 22, 1997, abandoned, all of which are herein incorporated by reference in their entirety.

2. FIELD OF THE INVENTION

The present invention provides novel polynucleotides and proteins encoded by such polynucleotides, along with therapeutic, diagnostic and research utilities for these polynucleotides and proteins.

3. BACKGROUND

Technology aimed at the discovery of protein factors (including e.g., cytokines, such as lymphokines, interferons, CSFs and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization cloning techniques, have advanced the state of the art by making available large numbers of DNA/amino acid sequences for proteins that are known to have biological activity by virtue of their secreted nature in the case of leader sequence cloning, or by virtue of the cell or tissue source in the case of PCR-based techniques. It is to these proteins and the polynucleotides encoding them that the present invention is directed.

Meningiomas are brain tumors formed from cells of the meninges, which are membranes that cover the brain and spinal cord. Meningiomas are relatively common and account for roughly half of all primary tumors of the brain and spinal cord. They are generally benign and slow growing, but may cause serious neurological problems due to invasion of or pressure on surrounding brain tissue. Treatment options include surgical removal and radiation therapy.

Astrocytomas are brain tumors formed from astrocytes, a type of brain glial cell that provides physical and nutritional support to the neurons of the brain. Astrocytomas are also a common tumor of brain tissue origin and may vary in aggressiveness, from the very aggressive glioblastoma multiforme, to the moderately aggressive anaplastic astrocytoma, to the least aggressive astrocytoma. They spread by infiltrating surrounding brain tissue but usually do not metastasize to other parts of the body. Treatment options include surgical removal, radiation therapy and chemotherapy, but complete surgical removal is typically difficult if not impossible due to the extensive infiltration of normal tissue.

Treatment options for cancer are of unpredictable and sometimes limited value, and there continues to exist a need for novel therapies and diagnostic methods for cancer conditions.

4. SUMMARY OF THE INVENTION

The compositions of the present invention include novel isolated polypeptides, in particular, novel EGF-repeat-containing polypeptides, isolated polynucleotides encoding such polypeptides, including recombinant DNA molecules, cloned genes or degenerate variants thereof, especially naturally occurring variants such as allelic variants, and antibodies that specifically recognize one or more epitopes present on such polypeptides.

The compositions of the present invention additionally include vectors, including expression vectors, containing the polynucleotides of the invention, cells genetically engineered to contain such polynucleotides and cells genetically engineered to express such polynucleotides.

The isolated polynucleotides of the invention include, but are not limited to, a polynucleotide encoding a polypeptide comprising the amino acid sequence of SEQ ID NOS: 3, or 6; a polynucleotide encoding a polypeptide comprising amino acid residues 1–502 of SEQ ID: 4 (The first amino acid residue in the sequence is designated as 1); a polynucleotide encoding a polypeptide comprising amino acid residues 1–21 of SEQ ID NOS: 6 or 24; a polynucleotide encoding a polypeptide comprising amino acid residues 80–93 of SEQ ID NOS: 6 or 24; a polynucleotide encoding a polypeptide comprising amino acid residues 95–128 of SEQ ID NOS: 6 or 24; a polynucleotide encoding a polypeptide comprising amino acid residues 133–168 of SEQ ID NOS: 6 or 24; a polynucleotide encoding a polypeptide comprising amino acid residues 175–214 of SEQ ID NOS: 6 or 24; a polynucleotide encoding a polypeptide comprising amino acid residues 220–259 of SEQ ID NOS: 6 or 24; a polynucleotide encoding a polypeptide comprising amino acid residues 446–465 of SEQ ID NOS: 6 or 24; or a polynucleotide encoding a polypeptide comprising amino acid residues 363–365 of SEQ ID NOS: 6 or 24.

The isolated polynucleotides of the invention further include, but are not limited to, a polynucleotide comprising the nucleotide sequence of SEQ ID NOS: 1, 2, 5 or 23; a polynucleotide comprising nucleotides 205–267 of the nucleotide sequence of SEQ ID NOS: 5 or 23 (The first nucleic acid residue of the sequence is designated as 1); a polynucleotide comprising nucleotides 442–483 of the nucleotide sequence of SEQ ID NOS: 5 or 23; a polynucleotide comprising nucleotides 487–588 of the nucleotide sequence of SEQ ID NOS: 5 or 23; a polynucleotide comprising nucleotides 601–708 of the nucleotide sequence of SEQ ID NOS: 5 or 23; a polynucleotide comprising nucleotides 727–846 of the nucleotide sequence of SEQ ID NOS: 5 or 23; a polynucleotide comprising nucleotides 862–981 of the nucleotide sequence of SEQ ID NOS: 5 or 23; a polynucleotide comprising nucleotides 1540–1599 of the nucleotide sequence of SEQ ID NOS: 5 or 23; a polynucleotide comprising nucleotides 1729–1731 of the nucleotide sequence of SEQ ID NOS: 5 or 23; or a polynucleotide comprising nucleotides 1291–1299 of the nucleotide sequence of SEQ ID NOS: 5 or 23.

The polynucleotides of the present invention still further include, but are not limited to, a polynucleotide comprising the nucleotide sequence of a cDNA insert of clone pEGFR-HY1 deposited with the American Type Culture Collection (ATCC; 10801 University Blvd., Manassas, Va., 20110-2209, U.S.A.); a polynucleotide comprising a nucleotide sequence of the cDNA insert of clone pEGFR-HY2 deposited with the ATCC; a polynucleotide comprising a nucleotide sequence of the cDNA insert of clone pEGFR-HY3 deposited with the ATCC; a polynucleotide comprising a nucleotide sequence encoding a polypeptide comprising the amino acid sequence encoded by the cDNA insert of clone pEGFR-HY1; a polynucleotide comprising a nucleotide sequence encoding a polypeptide comprising the amino acid sequence encoded by the cDNA insert of clone pEGFR-HY2; a polynucleotide comprising the nucleotide sequence encoding a polypeptide comprising the amino acid sequence encoded by the cDNA insert of clone pEGFR-HY3; a polynucleotide comprising the full length protein coding sequence of SEQ ID NOS: 6 or 24 which polynucleotide comprises the cDNA insert of clone pEGFR-HY2, nucleic acids 323–357 of SEQ ID NOS: 5 or 23 and the cDNA insert of clone pEGFR-HY1; a polynucleotide comprising the nucleotide sequence of the mature protein coding sequence of SEQ ID NOS: 6 or 24 comprising the cDNA insert of clone pEGFR-HY2, nucleic acids 323–357 of SEQ ID NOS: 5 or 23 and the cDNA insert of clone pEGFR-HY1; a polynucleotide comprising the fall length protein coding sequence of SEQ ID NOS: 6 or 24 which polynucleotide is assembled from the cDNA insert of clone pEGFR-HY2, the cDNA insert of pEGFR-HY3 and the cDNA insert of clone pEGFR-HY1; or a polynucleotide comprising the nucleotide sequence of the mature protein coding sequence of SEQ ID NOS: 6 or 24 which polynucleotide is assembled from the cDNA insert of clone pEGFR-HY2, the cDNA insert of clone pEGFR-HY3 and the cDNA insert of clone pEGFR-HY1. The polynucleotides of the present invention also include, but are not limited to, a polynucleotide that hybridizes to the complement of the nucleotide sequence of SEQ ID NOS: 1, 2, 5 or 23 under stringent hybridization conditions; a polynucleotide which is an allelic variant of any polynucleotide recited above; a polynucleotide which encodes a species homologue of any of the proteins recited above; or a polynucleotide that encodes a polypeptide comprising a specific domain or truncation of the polypeptide of SEQ ID NO: 3 or 6 or amino acids 1–502 of SEQ ID NO: 4.

The polynucleotides of the invention additionally include the complement of any of the polynucleotides recited above.

The isolated polypeptides of the invention include, but are not limited to, a polypeptide comprising the amino acid sequence of SEQ ID NOS: 3, 6 or 24; a polypeptide comprising amino acid residues 1–502 of SEQ ID NO: 4; a polypeptide comprising amino acid residues 1–21 of SEQ ID NOS: 6 or 24; a polypeptide comprising amino acid residues 80–93 of SEQ ID NOS: 6 or 24; a polypeptide comprising amino acid residues 95–128 of SEQ ID NOS: 6 or 24; a polypeptide comprising amino acid residues 133–168 of SEQ ID NOS: 6 or 24; a polypeptide comprising amino acid residues 175–214 of SEQ ID NOS: 6 or 24; a polypeptide comprising amino acid residues 220–259 of SEQ ID NOS: 6 or 24; a polypeptide comprising amino acid residues 446–465 of SEQ ID NOS: 6 or 24; or a polypeptide comprising amino acid residues 363–365 of SEQ ID NOS: 6 or 24. The polypeptide of SEQ ID NOS: 6 or 24 has been designated ERHy1.

The polypeptides of the present invention further include, but are not limited to, a polypeptide comprising the amino acid sequence encoded by the cDNA insert of clone pEGFR-HY1 deposited with the ATCC; a polypeptide comprising the amino acid encoded by the cDNA insert of clone pEGFR-HY2 deposited with the ATCC; a polypeptide comprising the amino acid encoded by the cDNA insert of clone pEGFR-HY3 deposited with the ATCC; a full length protein of SEQ ID NOS: 6 or 24 comprising the amino acid sequence encoded by the cDNA insert of clone pEGFR-HY2, nucleic acids 323–357 of SEQ ID NOS: 5 or 23 and the cDNA insert of clone pEGFR-HY1, or; a mature protein coding sequence of SEQ ID NOS: 6 or 24 comprising the amino acid sequence encoded by the cDNA insert of clone pEGFR-HY2, nucleic acids 323–357 of SEQ ID NOS: 5 or 23 and the cDNA insert of clone pEGFR-HY1. The polypeptides of the present invention also include, but are not limited to, a full length protein of SEQ ID NOS: 6 or 24 encoded by the open reading frame (ORF) assembled from the cDNA insert of clone pEGFR-HY2, the cDNA insert of clone pEGFR-HY3 and the cDNA insert of clone pEGFR-HY1; or a mature protein coding sequence of SEQ ID NOS: 6 or 24 encoded by the ORF assembled from the cDNA insert of clone pEGFR-HY2, the cDNA insert of clone pEGFR-HY3 and the cDNA insert of clone pEGFR-HY1.

Protein compositions of the present invention may further comprise an acceptable carrier, such as a hydrophilic, e.g., pharmaceutically acceptable, carrier.

The invention also relates to methods for producing a polypeptide comprising growing a culture of the cells of the invention in a suitable culture medium, and purifying the protein from the culture. Preferred embodiments include those in which the protein produced by such process is a mature form of the protein.

Polynucleotides according to the invention have numerous applications in a variety of techniques known to those skilled in the art of molecular biology. These techniques include use as hybridization probes, use as oligomers for PCR, use for chromosome and gene mapping, use in the recombinant production of protein, and use in generation of anti-sense DNA or RNA, their chemical analogs and the like. For example, when the expression of an mRNA is largely restricted to a particular cell or tissue type, polynucleotides of the invention can be used as hybridization probes to detect the presence of the particular cell or tissue mRNA in a sample using, e.g., in situ hybridization.

In other exemplary embodiments, the polynucleotides are used in diagnostics as expressed sequence tags for identifying expressed genes or, as well known in the art and exemplified by Vollrath et al., Science 258:52–59 (1992), as expressed sequence tags for physical mapping of the human genome.

The polypeptides according to the invention can be used in a variety of conventional procedures and methods that are currently applied to other proteins. For example, a polypeptide of the invention can be used to generate an antibody that specifically binds the polypeptide. The polypeptides of the invention having ATPase activity are also useful for inhibiting platelet aggregation and can therefore be employed in the prophylaxis or treatment of pathological conditions caused by the inflammatory response. The polypeptides of the invention can also be used as molecular weight markers, and as a food supplement.

Methods are also provided for preventing, treating or ameliorating a medical condition which comprises administering to a mammalian subject a therapeutically effective amount of a composition comprising a protein of the present invention and a pharmaceutically acceptable carrier.

In particular, the polypeptides and polynucleotides of the invention can be utilized, for example, as part of methods for stimulation of epithelial tissue growth, e.g., skin regeneration. The polypeptides and polynucleotides of the invention may, therefore, be utilized, for example, as part of methods for tissue repair and regeneration, corneal transplant healing, burn treatment, skin graft production and administration, and wound healing, e.g., treatment of surgical incisions, and ulcers, such as stomach or diabetic ulcers. In addition, the polynucleotides and polypeptides of the invention can further be utilized, for example, as part of methods for the prevention and/or treatment of disorders involving cell fate and differentiation, such as leukemias, brain tumors (including meningiomas, glioblastoma multiforme, anaplastic astrocytomas, cerebellar astrocytomas, other high-grade or low-grade astrocytomas, brain stem gliomas, oligodendrogliomas, mixed gliomas, other gliomas, cerebral neuroblastomas, craniopharyngiomas, diencephalic gliomas, germinomas, medulloblastomas, ependymomas, choroid plexus tumors, pineal parenchymal tumors, gangliogliomas, neuroepithelial tumors, neuronal and mixed neuronal glial tumors) and lung tumors (including small cell carcinomas, epidermoid carcinomas, adenocarcinomas, large cell carcinomas, carcinoid tumors, bronchial gland tumors, mesotheliomas, sarcomas and mixed tumors), as well as for the treatment of nervous disorders.

The methods of the present invention further relate to methods for detecting the presence of the polynucleotides or polypeptides of the invention in a sample. Such methods can, for example, be utilized as part of prognostic and diagnostic evaluation of disorders as recited above and for the identification of subjects exhibiting a predisposition to such conditions. Furthermore, the invention provides methods for evaluating the efficacy of drugs, and monitoring the progress of patients, involved in clinical trials for the treatment of disorders as recited above.

The ERHy1 protein of the present invention is expressed in certain cancer cells, particularly meningiomas and lung tumors, and has been localized to chromosome X, aberrations in which have been implicated in meningiomas and lung tumors. Other EGF motif-containing molecules have been previously linked to the progression of various cancers. Expression of ERHy1 in tumor cells indicates that this protein represents a potential marker of malignancy and a potential candidate for small molecule therapeutic development for the treatment of certain tumors.

Thus, the prognostic and diagnostic methods contemplated according to this aspect of the invention include methods of detecting or quantitating ERHy1 polypeptides in tissue samples (e g., biopsied tissue from brain, lung, or other tissues) or body fluid samples (e.g., cerebrospinal fluid, pleural fluid, sputum, ascites, blood, urine, or other fluids), particularly for diagnosis, prognosis or monitoring of cancer.

The invention also provides methods for the identification of compounds that modulate the expression of the polynucleotides and/or polypeptides of the invention. Such methods can be utilized, for example, for the identification of compounds that can ameliorate symptoms of disorders as recited above. Such methods can include, but are not limited to, assays for identifying compounds and other substances that interact with (e.g., bind to) the polypeptides of the invention.

The methods of the invention also include methods for the treatment of disorders as recited above which may involve the administration of such compounds to individuals exhibiting symptoms or tendencies related to disorders as recited above. In addition, the invention encompasses methods for treating diseases or disorders as recited above by administering compounds and other substances that modulate the overall activity of the target gene products. Compounds and other substances can effect such modulation either on the level of target gene expression or target protein activity.

The linkage of ERHy1 with cancer indicates that inhibitors of its activity (that either inhibit expression of the gene product or inhibit activity of the gene product itself) may be useful in treating cancer conditions. Such inhibitors include antisense polynucleotides, antibodies, and other modulators identified through, e.g., screening of libraries or combinatorial libraries of inorganic or organic compounds (such as bacterial, fungal, mammalian, insect or plant products, peptides, peptidomimetics and organomimetics). Such modulators may be administered parenterally, including into the CSF, or locally via an implant or device.

5. BRIEF DESCRIPTION OF THE DRAWINGS

FIG. 1 shows the sequence alignment of an EGF repeat containing portion of SEQ ID Nos. 6 or 24 (displayed sequence is SEQ ID NO: 9) with the consensus EGF-repeat motifs of drosophila Notch (SEQ ID NO: 7), CD97 (SEQ ID NO: 10), and the consensus EGF-R repeat (SEQ ID NO: 11). A-Alanine; R-Arginine; N-Asparagine; D-Aspartic Acid; C-Cysteine; E-Glutamic Acid; Q-Glutamine; G-Glycine; H-Histidine; I-Isoleucine; L-Leucine; K-Lysine; M-Methionine; F-Phenylalanine; P-Proline; S-Serine; T-Threonine; W-Tryptophan; Y-Tyrosine; V-Valine; X- any of the twenty amino acids. Gaps are presented as spaces and nonconserved residues as dashes. Regions of SEQ ID No. 4 are labeled 10244 (SEQ ID NO: 8). Amino acid positions for location of the beginning of each protein stretch are provided. Notch, CD97, and EGF-R are labeled accordingly. Consensus sequences are labeled (C). The conserved cysteines and glycines are underlined.

FIG. 2 shows the nucleic acid sequences that were obtained from the $b^2$HFLS20W cDNA library using standard PCR, sequencing by hybridization signature analysis, and single pass gel sequencing technology. These sequences are designated as SEQ ID Nos. 1–2. A-adenosine; C-cytosine; G-guanosine; T-thymidine; and N- any of the four bases.

FIG. 3 shows SEQ ID NOS:3–4. The amino acid sequence of SEQ ID NO: 3 corresponds to the polynucleotide sequence of SEQ ID NO: 1. (The amino acid sequence of SEQ ID NO: 18 corresponds to the polynucleotide sequence of SEQ ID NO: 2.) Amino acid residues 1–502 of SEQ ID NO:4 correspond to the polynucleotide sequence of SEQ ID NO:2 and to amino acid positions 52–553 of of SEQ ID NO 6 (see FIG. 5). A-Alanine; R-Arginine; N-Asparagine; D-Aspartic Acid; C-Cysteine; E-Glutamic Acid; Q-Glutamine; G-Glycine; H-Histidine; I-Isoleucine; L-Leucine; K-Lysine; M-Methionine; F-Phenylalanine; P-Proline; S-Serine; T-Threonine; W-Tryptophan; Y-Tyrosine; V-Valine; X- any of the twenty amino acids.

FIG. 4 shows SEQ ID NO. 5, which is a five prime and three prime extension of the cDNA sequence, SEQ ID NO. 2. Resequencing of pEGFR-HY2 and pEGFR-HY3 indicated an error in SEQ ID NO: 5 as presented in FIG. 4. Nucleotide 224 was reported to be a cytosine (C) in SEQ ID NO: 5 but should be a thymidine (T). The correct sequence is presented as SEQ ID NO: 23.

FIG. 5 shows the amino-acid translation (SEQ ID NOS: 6 or 24) from nucleotide 205 to 1866 of SEQ ID NO. 5, including the starting methionine and stop codon. The first 21 amino-acids comprise the hydrophobic region that represents the signal peptide. The sequencing error described above caused an error in the translated amino acid sequence shown in SEQ ID NO: 6 where a proline residue was reported at amino acid position 14. The corrected nucleotide sequence (SEQ ID NO: 23) resulted in a serine at position 14 and an isoleucine at position 357. The corrected nucleotide sequence is presented as SEQ ID NO: 24.

6. DETAILED DESCRIPTION

6.1. DEFINITIONS

The term "nucleotide sequence" refers to a heteropolymer of nucleotides or the sequence of these nucleotides. The terms "nucleic acid" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "oligonucleotide fragment" or a "polynucleotide fragment", "portion," or "segment" is a stretch of polypeptide nucleotide residues which is long enough to use in polymerase chain reaction (PCR) or various hybridization procedures to identify or amplify identical or related parts of mRNA or DNA molecules.

The terms "oligonucleotides" or "nucleic acid probes" are prepared based on the polynucleotide sequences provided in the present invention. Oligonucleotides comprise portions of such a polynucleotide sequence having at least about 15 nucleotides and usually at least about 20 nucleotides. Nucleic acid probes comprise portions of such a polynucleotide sequence having fewer nucleotides than about 6 kb, usually fewer than about 1 kb. After appropriate testing to eliminate false positives, these probes may, for example, be used to determine whether specific mRNA molecules are present in a cell or tissue or to isolate similar nucleic acid sequences from chromosomal DNA as described by Walsh et al. (Walsh, P. S. et al., 1992, PCR Methods Appl 1:241–250).

The term "probes" includes naturally occurring or recombinant or chemically synthesized single- or double-stranded nucleic acids. They may be labeled by nick translation, Klenow fill-in reaction, PCR or other methods well known in the art. Probes of the present invention, their preparation and/or labeling are elaborated in Sambrook, J. et al., 1989, Molecular Cloning: A Laboratory Manual, Cold Spring Harbor Laboratory, NY; or Ausubel, F. M. et al., 1989, Current Protocols in Molecular Biology, John Wiley & Sons, New York N.Y., both of which are incorporated herein by reference in their entirety.

The term "stringent is used to refer to conditions that are commonly understood in the art as stringent. Stringent conditions can include highly stringent conditions (i.e., hybridization to filter-bound DNA under in 0.5 M NaHPO$_4$, 7% sodium dodecyl sulfate (SDS), 1 mM EDTA at 65° C., and washing in 0.1×SSC/0.1% SDS at 68° C.), and moderately stringent conditions (i.e., washing in 0.2×SSC/0.1% SDS at 42° C.).

In instances wherein hybridization of deoxyoligonucleotides is concerned, additional exemplary stringent hybridization conditions include washing in 6×SSC/0.05% sodium pyrophosphate at 37° C. (for 14-base oligos), 48° C. (for 17-base oligos), 55° C. (for 20-base oligos), and 60° C. (for 23-base oligos).

The term "recombinant," when used herein to refer to a polypeptide or protein, means that a polypeptide or protein is derived from recombinant (e.g., microbial or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *E. coli*, will be free of glycosylation modifications; polypeptides or proteins expressed in yeast will have a glycosylation pattern in general different from those expressed in mammalian cells.

The term "recombinant expression vehicle or vector" refers to a plasmid or phage or virus or vector, for expressing a polypeptide from a DNA (RNA) sequence. An expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems as defined herein will express heterologous polypeptides or proteins upon induction of the regulatory elements linked to the DNA segment or synthetic gene to be expressed. This term also means host cells which have stably integrated a recombinant genetic element or elements having a regulatory role in gene expression, for example, promoters or enhancers. Recombinant expression systems as defined herein will express polypeptides or proteins endogenous to the cell upon induction of the regulatory elements linked to the endogenous DNA segment or gene to be expressed. The cells can be prokaryotic or eukaryotic.

The term "open reading frame," ORF, means a series of nucleotide triplets coding for amino acids without any termination codons and is a sequence translatable into protein.

The term "expression modulating fragment," EMF, means a series of nucleotides which modulates the expression of an operably linked ORF or another EMF.

As used herein, a sequence is said to "modulate the expression of an operably linked sequence" when the expression of the sequence is altered by the presence of the EMF. EMFs include, but are not limited to, promoters, and promoter modulating sequences (inducible elements). One class of EMFs are fragments which induce the expression or an operably linked ORF in response to a specific regulatory factor or physiological event.

As used herein, an "uptake modulating fragment," UMF, means a series of nucleotides which mediate the uptake of a linked DNA fragment into a cell. UMFs can be readily identified using known UMFs as a target sequence or target motif with the computer-based systems described below.

The presence and activity of a UMF can be confirmed by attaching the suspected UMF to a marker sequence. The resulting nucleic acid molecule is then incubated with an appropriate host under appropriate conditions and the uptake of the marker sequence is determined. As described above, a UMF will increase the frequency of uptake of a linked marker sequence.

The term "active" refers to those forms of the polypeptide which retain the biologic and/or immunologic activities of any naturally occurring polypeptide.

The term "naturally occurring polypeptide" refers to polypeptides produced by cells that have not been genetically engineered and specifically contemplates various polypeptides arising from post-translational modifications of the polypeptide including, but not limited to, acetylation, carboxylation, glycosylation, phosphorylation, lipidation and acylation.

The term "derivative" refers to polypeptides chemically modified by such techniques as ubiquitination, labeling (e.g., with radionuclides or various enzymes), pegylation (derivatization with polyethylene glycol) and insertion or substitution by chemical synthesis of amino acids such as ornithine, which do not normally occur in human proteins.

The term "recombinant variant" refers to any polypeptide differing from naturally occurring polypeptides by amino acid insertions, deletions, and substitutions, created using recombinant DNA techniques. Guidance in determining which amino acid residues may be replaced, added or deleted without abolishing activities of interest, such as cellular trafficking, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, non-polar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

As used herein, "substantially equivalent" can refer both to nucleotide and amino acid sequences, for example a mutant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 20% (i.e., the number of individual residue substitutions, additions, and/or deletions in a substantially equivalent sequence, as compared to the corresponding reference sequence, divided by the total number of residues in the substantially equivalent sequence is about 0.2 or less). Such a sequence is said to have 80% sequence identity to the listed sequence. In one embodiment, a substantially equivalent, e.g., mutant, sequence of the invention varies from a listed sequence by no more than 10% (90% sequence identity); in a variation of this embodiment, by no more than 5% (95% sequence identity); and in a further variation of this embodiment, by no more than 2% (98% sequence identity). Substantially equivalent, e.g., mutant, amino acid sequences according to the invention generally have at least 95% sequence identity with a listed amino acid sequence, whereas substantially equivalent nucleotide sequence of the invention can have lower percent sequence identities, taking into account, for example, the redundancy or degeneracy of the genetic code. For the purposes of the present invention, sequences having substantially equivalent biological activity and substantially equivalent expression characteristics are considered substantially equivalent. For the purposes of determining equivalence, truncation of the mature sequence (e.g., via a mutation which creates a spurious stop codon) should be disregarded.

Nucleic acid sequences encoding such substantially equivalent sequences, e.g., sequences of the recited percent identities, can routinely be isolated and identified via standard hybridization procedures well known to those of skill in the art.

Where desired, an expression vector may be designed to contain a "signal or leader sequence" which will direct the polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any polypeptide must have sufficient length to display biologic and/or immunologic activity.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

The term "activated" cells as used in this application are those which are engaged in extracellular or intracellular membrane trafficking, including the export of neurosecretory or enzymatic molecules as part of a normal or disease process.

The term "purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and purified" do not encompass nucleic acids or polypeptides present in their natural source.

The term "infection" refers to the introduction of nucleic acids into a suitable host cell by use of a virus or viral vector.

The term "transformation" means introducing DNA into a suitable host cell so that the DNA is replicable, either as an extrachromosomal element, or by chromosomal integration.

The term "transfection" refers to the taking up of an expression vector by a suitable host cell, whether or not any coding sequences are in fact expressed.

The term "intermediate fragment" means a nucleic acid between 5 and 1000 bases in length, and preferably between 10 and 40 bp in length.

The term "secreted" protein includes a protein that is transported across or through a membrane, including transport as a result of signal sequences in its amino acid sequence when it is expressed in a suitable host cell. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum.

Each of the above terms is meant to encompasses all that is described for each, unless the context dictates otherwise.

6.2 NUCLEIC ACIDS AND POLYPEPTIDES OF THE INVENTION

Nucleotide and amino acid sequences of the invention are reported below. Fragments of the proteins of the present invention which are capable of exhibiting biological activity are also encompassed by the present invention. Fragments of the protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein-IgM fusion would generate a decavalent form of the protein of the invention.

The present invention also provides both full-length and mature forms (for example, without a hydophobic signal peptide) of the disclosed proteins. The full-length form of the such proteins is identified in the sequence listing by translation of the nucleotide sequence of each disclosed clone. The mature form of such protein may be obtained by expression of the disclosed full-length polynucleotide (for example, obtained from using the clones deposited with ATCC using standard techniques) in a suitable mammalian cell or other host cell. The sequence of the mature form of the protein is also determinable from the amino acid sequence of the full-length form.

The present invention also provides genes corresponding to the cDNA sequences disclosed herein. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials.

Where the protein of the present invention is membrane-bound (e.g., is a receptor), the present invention also provides for soluble forms of such protein. In such forms part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information.

Species homologs of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or related to that encoded by the polynucleotides.

The compositions of the present invention include isolated polynucleotides, including recombinant DNA molecules, cloned genes or degenerate variants thereof, especially naturally occurring variants such as allelic variants, novel isolated polypeptides, and antibodies that specifically recognize one or more epitopes present on such polypeptides.

Species homologs of the disclosed polynucleotides and proteins are also provided by the present invention. Species homologs may be isolated and identified by making suitable probes or primers from the sequences provided herein and screening a suitable nucleic acid source from the desired species.

The invention also encompasses allelic variants of the disclosed polynucleotides or proteins; that is, naturally-occurring alternative forms of the isolated polynucleotide which also encode proteins which are identical, homologous or related to that encoded by the polynucleotides.

6.2.1. NUCLEIC ACIDS OF THE INVENTION

The isolated polynucleotides of the invention include, but are not limited to polynucleotides encoding a polypeptide comprising the amino acid sequence of SEQ ID NOS: 3, 6 or 24 or amino acid residues 1–502 of SEQ ID NO: 4 as well as polynucleotides which encode specific domains thereof For example, a polynucleotide encoding a polypeptide comprising amino acid residues 1–21 of SEQ ID NOS: 6 or 24; a polynucleotide encoding a polypeptide comprising amino acid residues 80–93 of SEQ ID NOS: 6 or 24; a polynucleotide encoding a polypeptide comprising amino acid residues 95–128 of SEQ ID NOS: 6 or 24; a polynucleotide encoding a polypeptide comprising amino acid residues 133–168 of SEQ ID NOS: 6 or 24; a polynucleotide encoding a polypeptide comprising amino acid residues 175–214 of SEQ ID NOS: 6 or 24; a polynucleotide encoding a polypeptide comprising amino acid residues 220–259 of SEQ ID NOS: 6 or 24; a polynucleotide encoding a polypeptide comprising amino acid residues 446–465 of SEQ ID NOS: 6 or 24; or a polynucleotide encoding a polypeptide comprising amino acid residues 363–365 of SEQ ID NOS: 6 or 24.

In particular embodiments, the isolated polynucleotides of the invention include, but are not limited to, a polynucleotide comprising the nucleotide sequence of SEQ ID NOS:1, 2, or 5; a polynucleotide comprising nucleotides 205–267 of the nucleotide sequence of SEQ ID NOS: 5 or 23; a polynucleotide comprising nucleotides 442–483 of the nucleotide sequence of SEQ ID NOS: 5 or 23; a polynucleotide comprising nucleotides 487–588 of the nucleotide sequence of SEQ ID NOS: 5 or 23; a polynucleotide comprising nucleotides 601–708 of the nucleotide sequence of SEQ ID NOS: 5 or 23; a polynucleotide comprising nucleotides 727–846 of the nucleotide sequence of SEQ ID NOS: 5 or 23; a polynucleotide comprising nucleotides 862–981 of the nucleotide sequence of SEQ ID NOS: 5 or 23; a polynucleotide comprising nucleotides 1540–1599 of the nucleotide sequence of SEQ ID NOS: 5 or 23; a polynucleotide comprising nucleotides 1729–1731 of the nucleotide sequence of SEQ ID NOS: 5 or 23; or a polynucleotide comprising nucleotides 1291–1299 of the nucleotide sequence of SEQ ID NOS: 5 or 23.

The polynucleotides of the present invention still further include, but are not limited to, a polynucleotide comprising the nucleotide sequence of the cDNA insert of clone pEGFR-HY1 deposited with the ATCC; a polynucleotide comprising the nucleotide sequence of the cDNA insert of clone pEGFR-HY2 deposited with the ATCC; a polynucleotide comprising the nucleotide sequence of the cDNA insert of clone pEGFR-HY3 deposited with the ATCC; a polynucleotide comprising the nucleotide sequence encoding a polypeptide comprising the amino acid sequence encoded by the cDNA insert of clone pEGFR-HY1; a polynucleotide comprising the nucleotide sequence encoding a polypeptide comprising the amino acid sequence encoded by the cDNA insert of clone pEGFR-HY2; a polynucleotide comprising the nucleotide sequence encoding a polypeptide comprising the amino acid sequence encoded by the cDNA insert of clone pEGFR-HY3; a polynucleotide comprising the full length protein coding sequence of SEQ ID NOS: 6 or 24 which polynucleotide comprises the cDNA insert of clone pEGFR-HY2, nucleic acids 323–357 of SEQ ID NOS: 5 or 23 and the cDNA insert of clone pEGFR-HY1; a polynucleotide comprising the nucleotide sequence of the mature protein coding sequence of SEQ ID NOS: 6 or 24 which polynucleotide comprises the cDNA insert of clone pEGFR-HY2, nucleic acids 323–357 of SEQ ID NOS: 5 or 23 and the cDNA insert of clone pEGFR-HY1; a polynucleotide comprising the full length protein coding sequence of SEQ ID NOS: 6 or 24 which polynucleotide is assembled from the the cDNA insert of clone pEGFR-HY2, the cDNA insert of clone pEGFR-HY3 and the cDNA insert of clone pEGFR-HY1,or; a polynucleotide comprising the nucleotide sequence of the mature protein coding sequence of SEQ ID NOS: 6 or 24 which polynucleotide is assembled from the cDNA insert of clone pEGFR-HY2, the cDNA insert of clone pEGFR-HY3 and the cDNA insert of clone pEGFR-HY1.

The polynucleotides of the present invention also include, but are not limited to, a polynucleotide that hybridizes to the complement of the nucleotide sequence of SEQ ID NOS: 1, 2, 5 or 23 under stringent hybridization conditions; a polynucleotide which is an allelic variant of any polynucleotide recited above; a polynucleotide which encodes a species homologue of any of the proteins recited above; or a polynucleotide that encodes a polypeptide comprising an additional specific domain or truncation of the polypeptide of SEQ ID NOS: 3, 6 or 24, or amino acid residues 1–502 of SEQ ID NO:4.

The polynucleotides of the invention additionally include the complement of any of the polynucleotides recited above.

The polynucleotides of the invention also provide polynucleotides including nucleotide sequences that are substantially equivalent to the polynucleotides recited above. Polynucleotides according to the invention can have at least about 80%, more typically at least about 90%, and even more typically at least about 95%, sequence identity to a polynucleotide recited above. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

A polynucleotide according to the invention can be joined to any of a variety of other nucleotide sequences by well-established recombinant DNA techniques (see Sambrook J et al. (1989) Molecular Cloning: A Laboratory Manual, Cold Spring Harbor Laboratory, NY). Useful nucleotide sequences for joining to polypeptides include an assortment of vectors, e.g., plasmids, cosmids, lambda phage derivatives, phagemids, and the like, that are well known in the art. Accordingly, the invention also provides a vector including a polynucleotide of the invention and a host cell containing the polynucleotide. In general, the vector contains an origin of replication functional in at least one organism, convenient restriction endonuclease sites, and a selectable marker for the host cell. Vectors according to the invention include expression vectors, replication vectors, probe generation vectors, and sequencing vectors. A host cell according to the invention can be a prokaryotic or eukaryotic cell and can be a unicellular organism or part of a multicellular organism.

The sequences falling within the scope of the present invention are not limited to the specific sequences herein described, but also include allelic variations thereof. Allelic variations can be routinely determined by comparing the sequence provided in SEQ ID NOS: 1, 2, 5 or 23, a representative fragment thereof, or a nucleotide sequence at least 99.9% identical to SEQ ID NOS: 1, 2, or 5, with a sequence from another isolate of the same species. Furthermore, to accommodate codon variability, the invention includes nucleic acid molecules coding for the same amino acid sequences as do the specific ORFs disclosed herein. In other words, in the coding region of an ORF, substitution of one codon for another which encodes the same amino acid is expressly contemplated. Any specific sequence disclosed herein can be readily screened for errors by resequencing a particular fragment, such as an ORF, in both directions (i.e., sequence both strands).

The present invention further provides recombinant constructs comprising a nucleic acid having the sequence of SEQ ID NOS: 1, 2, 5 or 23, or a fragment thereof. The recombinant constructs of the present invention comprise a vector, such as a plasmid or viral vector, into which a nucleic acid having the sequence of SEQ ID NOS: 1, 2, 5 or 23, or a fragment thereof is inserted, in a forward or reverse orientation. In the case of a vector comprising one of the ORFs of the present invention, the vector may further comprise regulatory sequences, including for example, a promoter, operably linked to the ORF. For vectors comprising the EMFs and UMFs of the present invention, the vector may further comprise a marker sequence or heterologous ORF operably linked to the EMF or UMF. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, PXTI, pSG (Stratagene) pSVK3, pBPV, pMSG, pSVL (Pharmacia).

The isolated polynucleotide of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art. Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product. Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced or derepressed by appropriate means (e.g., temperature shift or chemical induction) and cells are cultured for an additional period. Cells are typically harvested by centrifugation, disrupted by physical or chemical means, and the resulting crude extract retained for further purification.

Included within the scope of the nucleic acid sequences of the invention are nucleic acid sequences that hybridize under stringent conditions to a fragment of the DNA sequence in FIG. 2 or 4 or its complement, which fragment is greater than about 10 bp, preferably 20–50 bp, and even greater than 100 bp. In accordance with the invention, polynucleotide sequences which encode the novel nucleic acids, or functional equivalents thereof, may be used to generate recombinant DNA molecules that direct the expression of that nucleic acid, or a functional equivalent thereof, in appropriate host cells.

The nucleic acid sequences of the invention are further directed to sequences which encode variants of the described nucleic acids. These amino acid sequence variants may be prepared by methods known in the art by introducing appropriate nucleotide changes into a native or variant polynucleotide. There are two variables in the construction of amino acid sequence variants: the location of the mutation and the nature of the mutation. The amino acid sequence variants of the nucleic acids are preferably constructed by mutating the polynucleotide to give an amino acid sequence that does not occur in nature. These amino acid alterations can be made at sites that differ in the nucleic acids from different species (variable positions) or in highly conserved regions (constant regions). Sites at such locations will typically be modified in series, e.g., by substituting first with conservative choices (e.g., hydrophobic amino acid to a different hydrophobic amino acid) and then with more distant choices (e.g., hydrophobic amino acid to a charged amino acid), and then deletions or insertions may be made at the target site. Amino acid sequence deletions generally range from about 1 to 30 residues, preferably about 1 to 10 residues, and are typically contiguous. Amino acid insertions include amino- and/or carboxyl-terminal fusions ranging in length from one to one hundred or more residues, as well as intrasequence insertions of single or multiple amino acid residues. Intrasequence insertions may range generally from about 1 to 10 amino residues, preferably from 1 to 5 residues. Examples of terminal insertions include the heterologous signal sequences necessary for secretion or for intracellular targeting in different host cells.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., DNA 2:183 (1983). A versatile and efficient method for producing site-specific changes in a polynucleotide sequence was published by Zoller and Smith, Nucleic Acids Res. 10:6487–6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives the desired amino acid variant.

A further technique for generating amino acid variants is the cassette mutagenesis technique described in Wells et al., Gene 34:315 (1985); and other mutagenesis techniques well known in the art, such as, for example, the techniques in Sambrook et al., supra, and Current Protocols in Molecular Biology, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences include those which are capable of hybridizing to the appropriate novel nucleic acid sequence under stringent conditions.

6.2.2. HOSTS

The present invention further provides host cells genetically engineered to contain the polynucleotides of the invention. For example, such host cells may contain nucleic acids of the invention introduced into the host cell using known transformation, transfection or infection methods. The present invention still further provides host cells genetically engineered to express the polynucleotides of the invention, wherein such polynucleotides are in operative association with a regulatory sequence heterologous to the host cell which drives expression of the polynucleotides in the cell.

The host cell can be a higher eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected by calcium phosphate transfection, DEAE, dextran mediated transfection, or electroporation (Davis, L. et al., *Basic Methods in Molecular Biology* (1986)). The host cells containing one of polynucleotides of the invention, can be used in conventional manners to produce the gene product encoded by the isolated fragment (in the case of an ORF) or can be used to produce a heterologous protein under the control of the EMF.

Any host/vector system can be used to express one or more of the ORFs of the present invention. These include, but are not limited to, eukaryotic hosts such as HeLa cells, Cv-1 cell, COS cells, and Sf9 cells, as well as prokaryotic host such as *E. coli* and *B. subtilis*. The most preferred cells are those which do not normally express the particular polypeptide or protein or which expresses the polypeptide or protein at low natural level. Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., in *Molecular Cloning: A Laboratory Manual*, Second Edition, Cold Spring Harbor, N.Y. (1989), the disclosure of which is hereby incorporated by reference.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell tines. Mammalian expression vectors will comprise an origin of replication, a suitable promoter and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements. Recombinant polypeptides and proteins produced in bacterial culture are usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

In another embodiment of the present invention, cells and tissues may be engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. mRNA stability elements, splice sites, leader sequences for enhancing or modifying transport or secretion properties of the protein, or other sequences which alter or improve the function or stability of protein or RNA molecules.

The targeting event may be a simple insertion of the regulatory sequence, placing the gene under the control of the new regulatory sequence, e.g., inserting a new promoter or enhancer or both upstream of a gene. Alternatively, the targeting event may be a simple deletion of a regulatory element, such as the deletion of a tissue-specific negative regulatory element. Alternatively, the targeting event may replace an existing element; for example, a tissue-specific enhancer can be replaced by an enhancer that has broader or different cell-type specificity than the naturally occurring elements. Here, the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyl-transferase (gpt) gene.

The gene targeting or gene activation techniques which can be used in accordance with this aspect of the invention are more particularly described in U.S. Pat. No. 5,272,071 to Chappel; U.S. Pat. No. 5,578,461 to Sherwin et al.; International Application No. PCT/US92/09627 (WO93/09222) by Selden et al.; and International Application No. PCT/US90/06436 (WO91/06667) by Skoultchi et al., each of which is incorporated by reference herein in its entirety.

6.2.3. POLYPEPTIDES OF THE INVENTION

The isolated polypeptides of the invention include, but are not limited to, a polypeptide comprising the amino acid sequence of SEQ ID NOS: 3, 6 or 24 or amino acid residues 1–502 of SEQ ID NO: 4. The polypeptides of the invention further include polypeptides which comprise one or more specific domains of the amino acid sequence in SEQ ID NOS: 3, 6 or 24 or amino acid residues 1–502 of SEQ ID NO: 4. For example, but not limited to, a polypeptide comprising amino acid residues 1–21 of SEQ ID NOS: 6 or 24; a polypeptide comprising amino acid residues 80–93 of SEQ ID NOS: 6 or 24; a polypeptide comprising amino acid residues 95–128 of SEQ ID NOS: 6 or 24; a polypeptide comprising amino acid residues 133–168 of SEQ ID NOS: 6 or 24; a polypeptide comprising amino acid residues 175–214 of SEQ ID NOS: 6 or 24; a polypeptide comprising amino acid residues 220–259 of SEQ ID NOS: 6 or 24; a polypeptide comprising amino acid residues 446–465 of SEQ ID NOS: 6 or 24 or;a polypeptide comprising amino acid residues 363–365 of SEQ ID NOS: 6 or 24.

The polypeptides of the present invention further include, but are not limited to, a polypeptide comprising the amino acid sequence encoded by the cDNA insert of clone pEGFR-HY1 deposited with the ATCC; a polypeptide comprising the amino acid encoded by the cDNA insert of clone pEGFR-HY2 deposited with the ATCC; a polypeptide comprising the amino acid encoded by the cDNA insert of clone pEGFR-HY3 deposited with the ATCC; a full length protein coding sequence of SEQ ID NOS: 6 or 24 comprising the cDNA insert of clone pEGFR-HY2, nucleic acids 323–357 of SEQ ID NOS: 5 or 23 and the cDNA insert of clone pEGFR-HY1 or; a mature protein coding sequence of SEQ ID NOS: 6 or 24 comprising the cDNA insert of clone pEGFR-HY2, nucleic acids 323–357 of SEQ ID NOS: 6 or 24 and the cDNA insert of clone pEGFR-HY1. The polypeptides of the present invention also include, but are not limited to, a full length protein of SEQ ID NOS: 6 or 24 encoded by the open reading frame (ORF) assembled from the cDNA insert of clone pEGFR-HY2, the cDNA insert of clone pEGFR-HY3 and the cDNA insert of clone pEGFR-HY1; or a mature protein coding sequence of SEQ ID NOS: 6 or 24 encoded by the ORF assembled from the cDNA insert of clone pEGFR-HY2, the cDNA insert of clone pEGFR-HY3 and the cDNA insert of clone pEGFR-HY1.

Protein compositions of the present invention may further comprise an acceptable carrier, such as a hydrophilic, e.g., pharmaceutically acceptable, carrier.

The invention also relates to methods for producing a polypeptide comprising growing a culture of the cells of the invention in a suitable culture medium, and purifying the protein from the culture. For example, the methods of the invention include a process for producing a polypeptide in which a host cell containing a suitable expression vector that includes a polynucleotide of the invention is cultured under conditions that allow expression of the encoded polypeptide. The polypeptide can be recovered from the culture, conveniently from the culture medium, and further purified. Preferred embodiments include those in which the protein produced by such process is a full length or mature form of the protein.

The invention further provides a polypeptide including an amino acid sequence that is substantially equivalent to SEQ ID NOS: 3, 6 or 24 or amino acid residues 1–502 of SEQ ID NO:4. Polypeptides according to the invention can have at least about 95%, and more typically at least about 98%, sequence identity to SEQ ID NO:3 or 6 or amino acid residues 1–502 of SEQ ID NO: 4.

The present invention further provides isolated polypeptides encoded by the nucleic acid fragments of the present invention or by degenerate variants of the nucleic acid fragments of the present invention. By "degenerate variant" is intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins. A variety of methodologies known in the art can be utilized to obtain any one of the isolated polypeptides or proteins of the present invention. At the simplest level, the amino acid sequence can be synthesized using commercially available peptide synthesizers. This is particularly useful in producing small peptides and fragments of larger polypeptides. Fragments are useful, for example, in generating antibodies against the native polypeptide. In an alternative method, the polypeptide or protein is purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., *Scopes, Protein Purification: Principles and Practice*, Springer-Verlag (1994); Sambrook, et al., in *Molecular Cloning: A Laboratory Manual*; Ausubel et al., *Current Protocols in Molecular Biology*.

The polypeptides and proteins of the present invention can alternatively be purified from cells which have been altered to express the desired polypeptide or protein. As used herein, a cell is said to be altered to express a desired polypeptide or protein when the cell, through genetic manipulation, is made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention. The purified polypeptides can be used in in vitro binding assays which are well known in the art to identify molecules which bind to the polypeptides. These molecules include but are not limited to, for e.g., small molecules, molecules from combinatorial libraries, antibodies or other proteins. The molecules identified in the binding assay are then tested for antagonist or agonist activity in in vivo tissue culture or animal models that are well known in the art. In brief, the molecules are titrated into a plurality of cell cultures or animals and then tested for either cell/animal death or prolonged survival of the animal/cells.

In addition, the binding molecules maybe complexed with toxins, e.g., ricin or cholera, or with other compounds that are toxic to cells. The toxin-binding molecule complex is then targeted to a tumor or other cell by the specificity of the binding molecule for SEQ ID NOS: 3, 6 or 24 or amino acid residues 1–502 of SEQ ID NO: 4.

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MAXBAT™ kit), and such methods are well known in the art, as described in Summers and Smith, Texas Agricultural Experiment Station Bulletin No. 1555 (1987), incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, HEPARIN-TOYOPEARL.™. or CIBACROM BLUE 3GA SEPHAROSE.™.; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLab (Beverly, Mass.), Pharmacia (Piscataway, N.J.) and In Vitrogen, respectively. The protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

6.2.3. DEPOSIT OF CLONES

The clones, pEGFR-HY1 and pEGFR-HY2 were deposited with the American Type Culture Collection (ATCC) 10801 University Avenue, Manassas, Va., on Nov. 20, 1998 under the terms of the Budapest Treaty. The clone pEGFR-HY3 was deposited with the American Type Culture Collection (ATCC) 10801 University Avenue, Manassas, Va., on Nov. 25, 1998 under the terms of the Budapest Treaty. The cDNA insert of clone pEGFR-HY1 corresponds to nucleic acids 358–2365 of SEQ ID NOS: 5 or 23. The vector containing the cDNA insert is pT7T3D-pac; the cDNA insert is flanked by EcoR1 and Pac1 restriction sites. The cDNA insert of pEGFR-HY2 corresponds to nucleic acids 1–322 of SEQ ID NOS: 5 or 23. The vector containing the cDNA insert is pGEM®-T Easy Vector (Promega) with Marathon® cDNA Adaptor 2 Primer (Clontech) sequence attached to the 5' end. The cDNA insert is flanked by EcoRI sites. The clone pEGFR-HY3 was deposited the American Type Culture Collection (ATCC) 10801 University Avenue, Manassas, Va., on Nov. 20, 1998 under the terms of the Budapest Treaty. The cDNA insert of clone pEGFR-HY3 corresponds to nucleic acids 223 to 1193 of SEQ ID NO.: 5. The vector containing the cDNA insert is pGEM®-T Easy Vector (Promega) with Marathon® cDNA Adaptor 2 Primer (Clontech) sequence attached to the 5' end. The cDNA insert is flanked by EcoRI sites. The clones represent plasmid clones as described in the Examples set forth below.

| Microorganism/Clone | ATCC Accession No. |
|---|---|
| pEGFR-HY1 | 203492 |
| pEGFR-HY2 | 203493 |
| pEGFR-HY3 | 203498 |

6.3. USES AND BIOLOGICAL ACTIVITY

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

6.3.1. RESEARCH USES AND UTILITIES

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

6.3.2. NUTRITIONAL USES

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

6.3.3. CYTOKINE AND CELL PROLIFERATION/ DIFFERENTIATION ACTIVITY

A protein of the present invention may exhibit cytokine, cell proliferation (either inducing or inhibiting) or cell differentiation (either inducing or inhibiting) activity or may induce production of other cytokines in certain cell populations. A polynucleotide of the invention can encode a p6polypeptide exhibiting such attributes. Many protein factors discovered to date, including all known cytokines, have exhibited activity in one or more factor-dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123, T1165, HT2, CTLL2, TF-1, Mo7e and CMK. The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., I. Immunol. 149:3778–3783, 1992; Bowman et al., I. Immunol. 152:1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology, J. E. e.a. Coligan eds. Vol 1 pp. 3.12.1–3.12.14, John Wiley and Sons, Toronto. 1994; and Measurement of mouse and human interleukin gamma., Schreiber, R. D. In Current Protocols in Immunology. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In Current Protocols in Immunology. J. E. e.a. Coligan eds. Vol 1 pp. 6.6.1–6.6.5, John Wiley and Sons, Toronto. 1991; Smith et al., Proc. Natl. Aced. Sci. U.S.A. 83:1857–1861, 1986; Measurement of human Interleukin 11—Bennett, F., Giannotti, J., Clark, S. C. and Turner, K. J. In Current Protocols in Immunology. J. E. e.a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In Current Protocols in Immunology. J. B. e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

6.3.4. IMMUNE STIMULATING OR SUPPRESSING ACTIVITY

A protein of the present invention may also exhibit immune stimulating or immune suppressing activity, including without limitation the activities for which assays are described herein. A polynucleotide of the invention can encode a polypeptide exhibiting such activities. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by vital (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses maybe in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-vital immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient mounts of MHC class I or MHC class II molecules, can be transfected with nucleic acid encoding all or a portion of (e.g., a cytoplasmic-domain truncated portion) of an MHC class I .alpha. chain protein and .beta.sub.2 microglobulin protein or an MHC class II .alpha. chain protein and an MHC class II. beta. chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., I. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowmanet al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

6.3.5. HEMATOPOIESIS REGULATING ACTIVITY

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythoid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M. G. In Culture of Hematopoietic Cells. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In Culture of Hematopoietic Cells. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In Culture of Hematopoietic Cells. R. I. Freshney, et al. eds. Vol pp. 163–179, Wiley-Liss, Inc., New York, N.Y. 1994; Long term culture initiating cell assay, Sutherland, H. J. In Culture of Hematopoietic Cells. R. I. Freshney, et al. eds. Vol pp. 139–162, Wiley-Liss, Inc., New York, N.Y. 1994.

6.3.6. TISSUE GROWTH ACTIVITY

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-ike tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, Epidermal Wound Healing, pps. 71–112 (Maibach, H. I. and Rovee, D. T., eds.), Year Book Medical Publishers, Inc., Chicago, as modified by Eaglstein and Mertz, J. Invest. Dermatol 71:382–84 (1978).

6.3.7. ACTIVIN/INHIBIN ACTIVITY

A protein of the present invention may also exhibit activin- or inhibin-related activities. A polynucleotide of the invention may encode a polypeptide exhibiting such characteristics. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin $\alpha$-family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-$\beta$ group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

6.3.8. CHEMOTACTIC/CHEMOKINETIC ACTIVITY

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. A polynucleotide of the invention can encode a polypeptide exhibiting such attributes. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Marguiles, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25:1744–1748; Gruber et al. J. of Immunol. 152:5860–5867, 1994; Johnston et al. J. of Immunol. 153:1762–1768, 1994.

6.3.9. HEMOSTATIC AND THROMBOLYTIC ACTIVITY

A protein of the invention may also exhibit hemostatic or thrombolytic activity. A polynucleotide of the invention can encode a polypeptide exhibiting such attributes. Such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

6.3.10. RECEPTOR/LIGAND ACTIVITY

A protein of the present invention may also demonstrate activity as receptors, receptor ligands or inhibitors or agonists of receptor/ligand interactions. A polynucleotide of the invention can encode a polypeptide exhibiting such characteristics. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selecting, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

6.3.11. ANTI-INFLAMMATORY ACTIVITY

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation intimation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

6.3.12 LEUKEMIAS

Leukemias and related disorders may be treated or prevented by administration of a therapeutic that promotes or inhibits function of the polynucleotides and/or polypeptides of the invention. Such leukemias and related disorders include but are not limited to acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia and chronic lymphocytic leukemia (for a review of such disorders, see Fishman et al., 1985, *Medicine*, 2d Ed., J.B. Lippincott Co., Philadelphia).

6.3.13. NERVOUS SYSTEM DISORDERS

Nervous system disorders, involving cell types which can be tested for efficacy of intervention with compounds that modulate the activity of the polynucleotides and/or polypeptides of the invention, and which can be treated upon thus observing an indication of therapeutic utility, include but are not limited to nervous system injuries, and diseases or disorders which result in either a disconnection of axons, a diminution or degeneration of neurons, or demyelination. Nervous system lesions which may be treated in a patient (including human and non-human mammalian patients) according to the invention include but are not limited to the following lesions of either the central (including spinal cord, brain) or peripheral nervous systems:

(i) traumatic lesions, including lesions caused by physical injury or associated with surgery, for example, lesions which sever a portion of the nervous system, or compression injuries;

(ii) ischemic lesions, in which a lack of oxygen in a portion of the nervous system results in neuronal injury or death, including cerebral infarction or ischemia, or spinal cord infarction or ischemia;

(iii) malignant lesions, in which a portion of the nervous system is destroyed or injured by malignant tissue which is either a nervous system associated malignancy or a malignancy derived from non-nervous system tissue;

(iv) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis;

(v) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis;

(vi) lesions associated with nutritional diseases or disorders, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration;

(vii) neurological lesions associated with systemic diseases including but not limited to diabetes (diabetic neuropathy, Bell's palsy), systemic lupus erythematosus, carcinoma, or sarcoidosis;

(viii) lesions caused by toxic substances including alcohol, lead, or particular neurotoxins; and (ix) demyelinated lesions in which a portion of the nervous system is destroyed or injured by a demyelinating disease including but not limited to multiple sclerosis, human immunodeficiency virus-associated myelopathy, transverse myelopathy or various etiologies, progressive multifocal leukoencephalopathy, and central pontine myelinolysis.

Therapeutics which are useful according to the invention for treatment of a nervous system disorder may be selected by testing for biological activity in promoting the survival or differentiation of neurons. For example, and not by way of limitation, therapeutics which elicit any of the following effects may be useful according to the invention:

(i) increased survival time of neurons in culture;

(ii) increased sprouting of neurons in culture or in vivo;

(iii) increased production of a neuron-associated molecule in culture or in vivo, e.g., choline acetyltransferase or acetylcholinesterase with respect to motor neurons; or (iv) decreased symptoms of neuron dysfunction in vivo.

Such effects may be measured by any method known in the art. In preferred, non-limiting embodiments, increased survival of neurons may be measured by the method set forth in Arakawa et al. (1990, J. Neurosci. 10:3507–3515); increased sprouting of neurons may be detected by methods set forth in Pestronk et al. (1980, Exp. Neurol. 70:65–82) or Brown et al. (1981, Ann. Rev. Neurosci. 4:17–42); increased production of neuron-associated molecules may be measured by bioassay, enzymatic assay, antibody binding, Northern blot assay, etc., depending on the molecule to be measured; and motor neuron dysfunction may be measured by assessing the physical manifestation of motor neuron disorder, e.g., weakness, motor neuron conduction velocity, or functional disability.

In a specific embodiments, motor neuron disorders that may be treated according to the invention include but are not limited to disorders such as infarction, infection, exposure to toxin, trauma, surgical damage, degenerative disease or malignancy that may affect motor neurons as well as other components of the nervous system, as well as disorders that selectively affect neurons such as amyotrophic lateral sclerosis, and including but not limited to progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

6.3.14. OTHER ACTIVITIES

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, co-factors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin ike activity (such as, for example, the ability to bind antigens or complement); and the ability to act as an antigen in a vaccine composition to raise an immune response against such protein or another material or entity which is cross-reactive with such protein.

6.4. PHARMACEUTICAL FORMULATIONS AND ROUTES OF ADMINISTRATION

A protein of the present invention (from whatever source derived, including without limitation from recombinant and non-recombinant sources) may be administered to a patient in need, by itself, or in pharmaceutical compositions where it is mixed with suitable carriers or excipient(s) at doses to treat or ameliorate a variety of disorders. Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent. A protein of the present invention may be active in multimers (e.g., heterodimers or homodimers) or complexes with itself or other proteins. As a result, pharmaceutical compositions of the invention may comprise a protein of the invention in such multimeric or complexed form.

Techniques for formulation and administration of the compounds of the instant application may be found in "Remington's Pharmaceutical Sciences," Mack Publishing Co., Easton, Pa., latest edition. A therapeutically effective dose further refers to that amount of the compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or antithrombotic factors, or sequentially. If administered sequentially, the attending physician will decide on the appropriate sequence of administering protein of the present invention in combination with cytokine(s), lymphokine(s), other hematopoietic factor(s), thrombolytic or antithrombotic factors.

6.4.1. ROUTES OF ADMINISTRATION

Suitable routes of administration may, for example include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

Alternately, one may administer the compound in a local rather than systemic manner, for example, via injection of the compound directly into a arthritic joints or in fibrotic tissue, often in a depot or sustained release formulation. In order to prevent the scarring process frequently occurring as complication of glaucoma surgery, the compounds may be administered topically, for example, as eye drops.Furthermore, one may administer the drug in a targeted drug delivery system, for example, in a liposome coated with a specific antibody, targeting, for example, arthritic or fibrotic tissue. The liposomes will be targeted to and taken up selectively by the afflicted tissue.

6.4.2. COMPOSITIONS/FORMULATIONS

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes.Proper formulation is dependent upon the route of administration chosen. When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied for example. other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose. Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Many of the proteinase inhibiting compounds of the invention may be provided as salts with pharmaceutically compatible counterions. Such pharmaceutically acceptable base addition salts are those salts which retain the biological effectiveness and properties of the free acids and which are obtained by reaction with inorganic or organic bases such as sodium hydroxide, magnesium hydroxide, ammonia, trialkylamine, dialkylamine, monoalkylamine, dibasic amino acids, sodium acetate, potassium benzoate, triethanol amine and the like.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunoglobulin and other molecules on B cells as well as antibodies able to bind the TCR and other molecules on T cells can be combined with the pharmaceutical composition of the invention. The pharmaceutical composition of the invention may be in the form of a liposome in which protein of the present invention is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions used to practice the method of the present invention should contain about 0.01 $\mu$g to about 100 mg (preferably about 0.1 $\mu$g to about 10 mg, more preferably about 0.1 $\mu$g to about 1 mg) of protein of the present invention per kg body weight. For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material Is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability. Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylcelluloses), including methylcellulose, ethylcellulose, hydroxyethylcellulose, hydroxypropylcellulose, hydroxypropyl-methylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells. In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-.alpha. and TGF-.beta.), and insulin-like growth factor (IGF).

The therapeutic compositions are also presently valuable for veterinary applications. Particularly domestic animals and thoroughbred horses, in addition to humans, are desired patients for such treatment with proteins of the present invention. The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA). Cells may also be cultured ex vivo in the presence of proteins of the present invention in order to proliferate or to produce a desired effect on or activity in such cells. Treated cells can then be introduced in vivo for therapeutic purposes.

Delivery of a functional ERHy1 gene to appropriate cells may be effected ex vivo, in situ, or in vivo by use of vectors, and more particularly viral vectors (e.g., adenovirus, adeno-associated virus, or a retrovirus), or ex vivo by use of physical DNA transfer methods (e.g., liposomes or chemical treatments). See, for example, Anderson, Nature, supplement to vol. 392, no. 6679, pp. 25–20 (1998). For additional reviews of gene therapy technology see Friedmann, Science, 244: 1275–1281 (1989); Verma, Scientific American: 68–84 (1990); and Miller, Nature, 357: 455–460 (1992). Alternatively, it is contemplated that in other human disease states, preventing the expression of or inhibiting the activity of ERHy1 or mutants thereof will be useful in treating the disease states. It is contemplated that antisense therapy or gene therapy could be applied to negatively regulate the expression of ERHy1.

6.4.3. EFFECTIVE DOSAGE

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein. For any compound used in the method of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the C-proteinase activity). Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, in "The Pharmacological Basis of Therapeutics", Ch. 1 p.1. Dosage amount and interval may be adjusted individually to provide plasma levels of the active moiety which are sufficient to maintain the C-proteinase inhibiting effects, or minimal effective concentration (MEC). The MEC will vary for each compound but can be estimated from in vitro data; for example, the concentration necessary to achieve 50–90% inhibition of the C-proteinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%. In cases of local administration or selective uptake, the effective local concentration of the drug may not be related to plasma concentration.

The amount of composition administration will, of course, be departed on the subject being treated, on the subject's weight, the severity of the affliction, the manner of administration and the judgment of the prescribing physician.

6.4.4. PACKAGING

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

6.5. ANTIBODIES

Another aspect of the invention is an antibody that specifically binds the polypeptide of the invention. Such antibodies can be either monoclonal or polyclonal antibodies, as well fragments thereof and humanized forms or fully human forms, such as those produced in transgenic animals. The invention further provides a hybridoma that produces an antibody according to the invention. Antibodies of the invention are useful for detection and/or purification of the polypeptides of the invention.

Protein of the invention may also be used to immunize animals to obtain polyclonal and monoclonal antibodies which specifically react with the protein. Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987). Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein. In general, techniques for preparing polyclonal and monoclonal antibodies as well as hybridomas capable of producing the desired antibody are well known in the art (Campbell, A. M., Monoclonal Antibodies Technology: Laboratory Techniques in Biochemistry and Molecular Biology, Elsevier Science Publishers, Amsterdam, The Netherlands (1984); St. Groth et al., J. Immunol. 35:1–21 (1990); Kohler and Milstein, Nature 256:495–497 (1975)), the trioma technique, the human B-cell hybridoma technique (Kozbor et al., Immunology Today 4:72 (1983); Cole et al., in Monoclonal Antibodies and Cancer Therapy, Alan R. Liss, Inc. (1985), pp. 77–96).

Any animal (mouse, rabbit, etc.) which is known to produce antibodies can be immunized with a peptide or polypeptide of the invention. Methods for immunization are well known in the art. Such methods include subcutaneous or intraperitoneal injection of the polypeptide. One skilled in the art will recognize that the amount of the protein encoded by the ORF of the present invention used for immunization will vary based on the animal which is immunized, the antigenicity of the peptide and the site of injection. The protein that is used as an immunogen may be modified or administered in an adjuvant in order to increase the protein's antigenicity. Methods of increasing the antigenicity of a protein are well known in the art and include, but are not limited to, coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Research. 175:109–124 (1988)). Hybridomas secreting the desired antibodies are cloned and the class and subclass is determined using procedures known in the art (Campbell, A. M., Monoclonal Antibody Technology: Laboratory Techniques in Biochemistry and Molecular Biology, Elsevier Science Publishers, Amsterdam, The Netherlands (1984)). Techniques described for the production of single chain antibodies (U.S. Pat. No. 4,946,778) can be adapted to produce single chain antibodies to proteins of the present invention.

For polyclonal antibodies, antibody containing antiserum is isolated from the immunized animal and is screened for the presence of antibodies with the desired specificity using one of the above-described procedures. The present invention further provides the above-described antibodies in delectably labeled form. Antibodies can be delectably labeled through the use of radioisotopes, affinity labels (such as biotin, avidin, etc.), enzymatic labels (such as horseradish peroxidase, alkaline phosphatase, etc) fluorescent labels (such as FITC or rhodamine, etc.), paramagnetic atoms, etc. Procedures for accomplishing such labeling are well-known in the art, for example, see (Stemberger, L. A. et al., J. Histochem. Cytochem. 18:315 (1970); Bayer, E. A. et al., Meth. Enzym. 62:308 (1979); Engval, E. et al., Immunol. 109:129 (1972); Goding, J. W. J. Immunol. Meth. 13:215 (1976)).

The labeled antibodies of the present invention can be used for in vitro, in vivo, and in situ assays to identify cells or tissues in which a fragment of the polypeptide of interest is expressed. The antibodies may also be used directly in therapies or other diagnostics. The present invention further provides the above-described antibodies immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir, D. M. et al., "Handbook of Experimental Immunology" 4th Ed., Blackwell Scientific Publications, Oxford, England, Chapter 10 (1986); Jacoby, W. D. et al., Meth. Enzym. 34 Academic Press, N.Y. (1974)). The immobilized antibodies of the present invention can be used for in vitro, in vivo, and in situ assays as well as for immuno-affinity purification of the proteins of the present invention.

6.6. COMPUTER READABLE SEQUENCES

In one application of this embodiment, a nucleotide sequence of the present invention can be recorded on computer readable media. As used herein, "computer readable media" refers to any medium which can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention. As used herein, "recorded" refers to a process for storing information on computer readable medium. A skilled artisan can readily adopt any of the presently known methods for recording information on computer readable medium to generate manufactures comprising the nucleotide sequence information of the present invention.

A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of dataprocessor structuring formats (e.g. text file or database) in order to obtain computer readable medium having recorded thereon the nucleotide sequence information of the present invention. By providing the nucleotide sequence of SEQ ID NOS: 1, 2, 5 or 23 or a representative fragment thereof, or a nucleotide sequence at least 99.9% identical to SEQ ID NOS: 1, 2, 5 or 23 in computer readable form, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., J. Mol. Biol. 215:403–410 (1990)) and BLAZE (Brutlag et al., Comp. Chem. 17:203–207 (1993)) search algorithms on a Sybase system is used to identify open reading frames (ORFs) within a nucleic acid sequence. Such ORFs may be protein encoding fragments and may be useful in producing commercially important proteins such as enzymes used in fermentation reactions and in the production of commercially useful metabolites.

As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based systems are suitable for use in the present invention. As stated above, the computer-based systems of the present invention comprise a data storage means having stored therein a nucleotide sequence of the present invention and the necessary hardware means and software means for supporting and implementing a search means. As used herein, "data storage means" refers to memory which can store nucleotide sequence information of the present invention, or a memory access means which can access manufactures having recorded thereon the nucleotide sequence information of the present invention.

As used herein, "search means" refers to one or more programs which are implemented on the computer-based system to compare a target sequence or target structural motif with the sequence information stored within the data storage means. Search means are used to identify fragments or regions of a known sequence which match a particular target sequence or target motif. A variety of known algorithms are disclosed publicly and a variety of commercially available software for conducting search means are and can be used in the computer-based systems of the present invention. Examples of such software includes, but is not limited to, MacPattern (EMBL), BLASTN and BLASTA (NPOLYPEPTIDEIA). A skilled artisan can readily recognize that any one of the available algorithms or implementing software packages for conducting homology searches can be adapted for use in the present computer-based systems. As used herein, a "target sequence" can be any nucleic acid or amino acid sequence of six or more nucleotides or two or more amino acids. A skilled artisan can readily recognize that the longer a target sequence is, the less likely a target sequence will be present as a random occurrence in the database. The most preferred sequence length of a target sequence is from about 10 to 100 amino acids or from about 30 to 300 nucleotide residues. However, it is well recognized that searches for commercially important fragments, such as sequence fragments involved in gene expression and protein processing, may be of shorter length.

As used herein, "a target structural motif," or "target motif," refers to any rationally selected sequence or combination of sequences in which the sequence(s) are chosen based on a three-dimensional configuration which is formed upon the folding of the target motif. There are a variety of target motifs known in the art. Protein target motifs include, but are not limited to, enzyme active sites and signal sequences. Nucleic acid target motifs include, but are not limited to, promoter sequences, hairpin structures and inducible expression elements (protein binding sequences).

6.7. TRIPLE HELIX FORMATION

In addition, the fragments of the present invention, as broadly described, can be used to control gene expression through triple helix formation or antisense DNA or RNA, both of which methods are based on the binding of a polynucleotide sequence to DNA or RNA. Polynucleotides suitable for use in these methods are usually 20 to 40 bases in length and are designed to be complementary to a region of the gene involved in transcription (triple helix—see Lee et al., Nucl. Acids Res. 6:3073 (1979); Cooney et al., Science 15241:456 (1988); and Dervan et al., Science 251:1360 (1991)) or to the mRNA itself (antisense—Olmno, J. Neurochem. 56:560 (1991); Oligodeoxynucleotides as Antisense Inhibitors of Gene Expression, CRC Press, Boca Raton., Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide.

6.8. DIAGNOSTIC ASSAYS AND KITS

The present invention further provides methods to identify the presence or expression of one of the ORFs of the present invention, or homolog thereof, in a test sample, using a nucleic acid probe or antibodies of the present invention.

In general, methods for detecting a polynucleotide of the invention can comprise contacting a sample with a compound that binds to and forms a complex with the polynucleotide for a period sufficient to form the complex, and detecting the complex, so that if a complex is detected, a polynucleotide of the invention is detected in the sample. Such methods can also comprise contacting a sample under stringent hybridization conditions with nucleic acid primers that anneal to a polynucleotide of the invention under such conditions, and amplifying annealed polynucleotides, so that if a polynucleotide is amplified, a polynucleotide of the invention is detected in the sample.

In general, methods for detecting a polypeptide of the invention can comprise contacting a sample with a compound that binds to and forms a complex with the polypeptide for a period sufficient to form the complex, and detecting the complex, so that if a complex is detected, a polypeptide of the invention is detected in the sample.

In detail, such methods comprise incubating a test sample with one or more of the antibodies or one or more of nucleic acid probes of the present invention and assaying for binding of the nucleic acid probes or antibodies to components within the test sample.

Conditions for incubating a nucleic acid probe or antibody with a test sample vary. Incubation conditions depend on the format employed in the assay, the detection methods employed, and the type and nature of the nucleic acid probe or antibody used in the assay. One skilled in the art will recognize that any one of the commonly available hybridization, amplification or immunological assay formats can readily be adapted to employ the nucleic acid probes or antibodies of the present invention. Examples of such assays can be found in Chard, T., An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (1982), Vol. 2 (1983), Vol. 3 (1985); Tijssen, P., Practice and Theory of immunoassays: Laboratory Techniques in Biochemistry and Molecular Biology, Elsevier Science Publishers, Amsterdam, The Netherlands (1985). The test samples of the present invention include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is compatible with the system utilized.

In another embodiment of the present invention, kits are provided which contain the necessary reagents to carry out the assays of the present invention. Specifically, the invention provides a compartment kit to receive, in close confinement, one or more containers which comprises: (a) a first container comprising one of the probes or antibodies of the present invention; and (b) one or more other containers comprising one or more of the following: wash reagents, reagents capable of detecting presence of a bound probe or antibody.

In detail, a compartment kit includes any kit in which reagents are contained in separate containers. Such containers include small glass containers, plastic containers or strips of plastic or paper. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the antibodies used in the assay, containers which contain wash reagents (such as phosphate buffered saline, Tris-buffers, etc.), and containers which contain the reagents used to detect the bound antibody or probe. Types of detection reagents include labeled nucleic acid probes, labeled secondary antibodies, or in the alternative, if the primary antibody is labeled, the enzymatic, or antibody binding reagents which are capable of reacting with the labeled antibody. One skilled in the art will readily recognize that the disclosed probes and antibodies of the present invention can be readily incorporated into one of the established kit formats which are well known in the art.

6.9. SCREENING ASSAYS

Using the isolated proteins and polynucleotides of the invention, the present invention further provides methods of obtaining and identifying agents which bind to a polypeptide encoded by the ORF from a polynucleotide with a sequence of SEQ ID NOS: 1, 2, 5 or 23 to a specific domain of the polypeptide encoded by the nucleic acid, or to a nucleic acid with a sequence of SEQ ID NOS: 1, 2, 5 or 23. In detail, said method comprises the steps of:

(a) contacting an agent with an isolated protein encoded by an ORF of the present invention, or nucleic acid of the invention; and (b) determining whether the agent binds to said protein or said nucleic acid.

In general, therefore such methods for identifying compounds that bind to a polynucleotide of the invention can comprise contacting a compound with a polynucleotide of the invention for a time sufficient to form a polynucleotide/compound complex, and detecting the complex, so that if a polynucleotide/compound complex is detected, a compound that binds to a polynucleotide of the invention is identified.

Likewise, in general, therefore, such methods for identifying compounds that bind to a polypeptide of the invention can comprise contacting a compound with a polypeptide of the invention for a time sufficient to form a polypeptide/compound complex, and detecting the complex, so that if a polypeptide/compound complex is detected, a compound that binds to a polypeptide of the invention is identified.

Methods for identifying compounds that bind to a polypeptide of the invention can also comprise contacting a compound with a polypeptide of the invention in a cell for a time sufficient to form a polypeptide/compound complex, wherein the complex drives expression of a receptor gene sequence in the cell, and detecting the complex by detecting reporter gene sequence expression, so that if a polypeptide/compound complex is detected, a compound that binds a polypeptide of the invention is identified.

Compounds identified via such methods can include compounds which modulate the activity of a polypeptide of the invention (that is, increase or decrease its activity, relative to activity observed in the absence of the compound). Alternatively, compounds identified via such methods can include compounds which modulate the expression of a polynucleotide of the invention (that is, increase or decrease expression relative to expression levels observed in the absence of the compound). Compounds, such as compounds identified via the methods of the invention, can be tested using standard assays well known to those of skill in the art for their ability to modulate activity/expression.

The agents screened in the above assay can be, but are not limited to, peptides, carbohydrates, vitamin derivatives, or other pharmaceutical agents. The agents can be selected and screened at random or rationally selected or designed using protein modeling techniques.

For random screening, agents such as peptides, carbohydrates, pharmaceutical agents and the like are selected at random and are assayed for their ability to bind to the protein encoded by the ORF of the present invention. Alternatively, agents may be rationally selected or designed. As used herein, an agent is said to be "rationally selected or designed" when the agent is chosen based on the configuration of the particular protein. For example, one skilled in the art can readily adapt currently available procedures to generate peptides, pharmaceutical agents and the like capable of binding to a specific peptide sequence in order to generate rationally designed antipeptide peptides, for example see Hurby et al., Application of Synthetic Peptides: Antisense Peptides," In Synthetic Peptides, A User's Guide, W. H. Freeman, NY (1992), pp. 289–307, and Kaspczak et al., Biochemistry 28:9230–8 (1989), or pharmaceutical agents, or the like.

In addition to the foregoing, one class of agents of the present invention, as broadly described, can be used to control gene expression through binding to one of the ORFs or EMFs of the present invention. As described above, such agents can be randomly screened or rationally designed/selected. Targeting the ORF or EMF allows a skilled artisan to design sequence specific or element specific agents, modulating the expression of either a single ORF or multiple ORFs which rely on the same EMF for expression control. One class of DNA binding agents are agents which contain base residues which hybridize or form a triple helix formation by binding to DNA or RNA. Such agents can be based on the classic phosphodiester, ribonucleic acid backbone, or can be a variety of sulfhydryl or polymeric derivatives which have base attachment capacity.

Agents suitable for use in these methods usually contain 20 to 40 bases and are designed to be complementary to a region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988)). Triple helix-formation optimally results in a shut-off of RNA transcription from DNA, while antisense RNA hybridization blocks translation of an mRNA molecule into polypeptide. Both techniques have been demonstrated to be effective in model systems. Information contained in the sequences of the present invention is necessary for the design of an antisense or triple helix oligonucleotide and other DNA binding agents. Agents which bind to a protein encoded by one of the ORFs of the present invention can be used as a diagnostic agent, in the control of bacterial infection by modulating the activity of the protein encoded by the ORF. Agents which bind to a protein encoded by one of the ORFs of the present invention can be formulated using known techniques to generate a pharmaceutical composition.

6.10. USE OF NUCLEIC ACIDS AS PROBES

Another aspect of the subject invention is to provide for polypeptide-specific nucleic acid hybridization probes capable of hybridizing with naturally occurring nucleotide sequences. The hybridization probes of the subject invention may be derived from the nucleotide sequence of the SEQ ID NOS: 1, 2, 5 or 23. Because the corresponding gene is only expressed in a limited number of tissues, especially adult tissues, a hybridization probe derived from SEQ ID NOS: 1, 2, 5 or 23 can be used as an indicator of the presence of RNA of cell type of such a tissue in a sample.

Any suitable hybridization technique can be employed, such as, for example, in situ hybridization. PCR as described U.S. Pat. Nos. 4,683,195 and 4,965,188 provides additional uses for oligonucleotides based upon the nucleotide sequences. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for nucleic acids include the cloning of nucleic acid sequences into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides. The nucleotide sequences may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes A Manual of Basic Techniques, Pergamon Press, New York, N.Y.

Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a nucleic acid on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.The nucleotide sequence may be used to produce purified polypeptides using well known methods of recombinant DNA technology. Among the many publications that teach methods for the expression of genes after they have been isolated is Goeddel (1990) Gene Expression Technology, Methods and Enzymology, Vol 185, Academic Press, San Diego. Polypeptides may be expressed in a variety of host cells, either prokaryotic or eukaryotic. Host cells may be from the same species from which a particular polypeptide nucleotide sequence was isolated or from a different species. Advantages of producing polypeptides by recombinant DNA technology include obtaining adequate amounts of the protein for purification and the availability of simplified purification procedures.

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc., Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches Smith-Waterman alignments were used to display the results of the homology search. Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology that were scored with an initial value. Dot-matrix homology plots were examined to distinguish regions of significant homology from chance matches.

Alternatively, BLAST, which stands for Basic Local Alignment Search Tool, is used to search for local sequence alignments (Altschul SF (1993) J Mol Evol 36:290–300; Altschul, S F et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP). An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

In addition, BLAST analysis was used to search for related molecules within the libraries of the LIFESEQ™ database. This process, an "electronic northern" analysis is analogous to northern blot analysis in that it uses one cellubrevin sequence at a time to search for identical or homologous molecules at a set stringency. The stringency of the electronic northern is based on "product score". The product score is defined as (% nucleotide or amino acid [between the query and reference sequences] in Blast multiplied by the % maximum possible BLAST score [based on the lengths of query and reference sequences]) divided by 100. At a product score of 40, the match will be exact within a 1–2% error; and at 70, the match will be exact. Homologous or related molecules can be identified by selecting those which show product scores between approximately 15 and 30.

The present invention is illustrated in the following examples. Upon consideration of the present disclosure, one of skill in the art will appreciate that many other embodiments and variations may be made in the scope of the present invention. Accordingly, it is intended that the broader aspects of the present invention not be limited to the disclosure of the following examples.

7.0. EXAMPLES

7.1. EXAMPLE 1

A NOVEL NUCLEIC ACID SEQUENCE OBTAINED FROM A CDNA LIBRARY OF FETAL LIVER-SPLEEN ENCODING AN EGF-RECEPTOR LIKE PROTEIN.

A plurality of novel nucleic acids were obtained from the $b^2$HFLS20W cDNA library prepared from human fetal liver-spleen tissue, as described in Bonaldo et al., Genome Res. 6:791–806 (1996), using standard pcr, SBH sequence signature analysis and Sanger sequencing techniques. The inserts of the library were amplified with pcr using primers specific for vector sequences which flank the inserts. These samples were spotted onto nylon membranes and interrogated with oligonucleotide probes to give sequence signatures. The clones were clustered into groups of similar or identical sequences, and single representative clones were selected from each group for gel sequencing. The 5' sequence of the, amplified inserts was then deduced using the reverse M13 sequencing primer in a typical Sanger sequencing protocol. PCR products were purified and subjected to flourescent dye terminator cycle sequencing. Single pass gel sequencing was done using a 377 Applied Biosystems (ABI) sequencer. Two (2) of these inserts have been identifed as novel sequences not previously obtained from this library, and not previously reported in public databases. These sequences are shown in FIG. 2 as SEQ ID NO. 1–2. The polypeptide sequence corresponding to the nucleic acid sequence of SEQ ID NO: 1 is shown in FIG. 2 as SEQ ID NO: 3. The polypeptide sequence corresponding to SEQ ID NO: 2 is shown in FIG. 2 as amino acid residues 1–502 of SEQ ID NO: 4 as the designation "NNN" in SEQ ID NO: 2 represents a sequence ambiguity. These amino acid sequences contain EGF motifs that have striking homology to the EGF motifs of Notch (from drosophila) and CD97.

Epidermal growth factor and transforming growth factor transmit their signals for cellular growth through EGF-R via an intracellular tyrosine kinase domain. Signaling through EGF induces cell division. Mutated forms of EGF have been demonstrated to be involved in various cancers owing to a lack of regulation in cell division signaling (Carter et al., Crit Rev Oncog 1994; 5(4):389–428, Chrysogelos, et al., Breast Cancer Res Treat 1994 January; 29(1):29–40). This has provided the opportunity to use EGF and other ligands of EGF-R as therapeutic targets for human cancers (Rusch, et al., Cytokine Growth Factor Rev 1996 August; 7(2):133–141). Mice with targeted mutations to both alleles of the EGF receptor gene die very young after birth from multiorgan failure revealing EGF receptor as essential mammalian protein (Miettinen, et al., Nature 1995 July 27; 376():377–341). Notch is a receptor protein initially identified in drosophlia (Kidd, et al., Mol Cell Biol 1986 September; 6(9):3094–3108).

The Notch family of transmembrane receptor proteins are key developmental regulators. Mutations in mammalian Notch genes have been implicated in leukaemia, breast cancer, stroke and dementia (Panin, et al., Nature 1997 June 26; 387(6636):908–912). The extracellular domain of Notch contains 36 EGF-like repeats, a transmembrane domain and three other repetative elements (Kidd, et al., Mol Cell Biol 1986 September; 6(9):3094–3108).

CD97 is a surface molecule expressed mainly on leukocytes. It has five EGF-like domains and seven transmembrane domains, a defining feature of G protein-coupled receptors (Gray, et al., Journal of Immunology 1996 157:5438–5447). It also has a RGD motif (involved in binding to integrin molecules) and eight potential N-linked glycosylation sites. CD97 has links to cancer (it is a dedifferentiation marker of human thyroid carcinomas; Aust, et al., Cancer Res 1997 May 1; 57(9):1798–1806) and inflammation (Gray, et al., Journal of Immunology 1996 157:5438–5447).

7.2. EXAMPLE 2

EXPRESSION STUDIES WITH SEQ ID NOS 1–2.

To determine if SEQ. ID NO: 2 is expressed specifically in diseased or normal human tissues, a Northern blot analysis was performed. The entire cDNA insert was labelled with radioisotope using a multiprime labeling method. A high stringency wash was preformed to ensure specific hybridization. The resultant hybridization pattern produced a total of five different bands (approximately 6.5, 4.0, 2.1, 0.5 and 0.2 kb). Two of these bands (6.5 and 4 kb) were uniquely expressed in a sample derived from a brain tumor (astrocytoma of cerebellum) and not in a panel of samples from 19 other tissues (normal brain, kidney tumor and normal kidney, liver tumor and normal liver, lung tumor and normal lung, normal heart, pancreas spleen and skeletal muscle and fetal brain, liver, lung, and skeletal muscle). The other 3 bands were expressed to varying degrees in the other tissues. These results indicate that the two higher molecular weight bands are specific to the brain tumor tissue and not to the other samples surveyed. As EGF-motif containing receptors have been previously been linked to the progression of various cancers, we believe that the full length message to SEQ ID No. 2 is involved in brain tumor development.

In addition, cDNA libraries prepared from a wide variety of tissue types were surveyed for expression of SEQ ID NOS: 5 or 23 (ERHy1) using a screening by hybridization approach. The expression level (mRNA transcript frequency) of a gene is determined by dividing the number of clones corresponding to that gene (cluster size) by the total number of clones analyzed in the cDNA library survey. ERHy1 expression was detected only in lung tumor and a subset of fetal libraries at the following transcript frequencies: 0.003% of lung tumor (adenocarcinoma), 0.01% of fetal lung, 0.007% of fetal skin, 0.006% of fetal umbilical cord, 0.0035% of fetal liver-spleen and 0.0027% of placenta, with the total number of cDNA transcripts ranging from about 10 to 30 copies per cell in these six libraries. In contrast, none of the normal adult tissues, including lung, express ERHy1 transcript at a detectable level.

To expand the survey of tumor tissues, a further Northern blot analysis of mRNA from normal and cancer tissues was performed. To eliminate the possibility of cross-hybridizing to other EGF motif-containing sequences, the probe used was generated from sequences outside of the EGF repeat region (nucleotides 1105–1906 of SEQ ID NOS: 5 or 23). This 801 bp probe was amplified by PCR using gene specific primers (5'-CCAGAACCCACCAGGACTCC-3', SEQ ID NO: 21; 5'-GGGAACTGACATACAAAGTC-3'; SEQ ID NO: 22) and labeled using the Prime-IT® II Random Primer Labeling Kit from Stratagene (LA Jolla, Calif.) in the presence of [$^{33}$P]-α-dCTP. A high stringency hybridization and wash was performed to ensure specific hybridization, using the ExpressHyb™ hybridization solution (Clontech, Palo Alto, Calif.) according to the instructions of the manufacturer. A human multiple tissue Northern blot (Clontech) and a human brain tumor blot (Invitrogen, Carlsbad, Calif.) were tested. The results showed a single band (approximately 2.4 kb) expressed specifically in placenta and meningioma tumor tissues. All other normal tissues (brain, heart, skeletal muscle, colon, thymus, spleen, kidney, liver, small intestine, lung and peripheral blood leukocytes), glioma brain tumor tissue and malignant lymphoma tumor tissue did not yield a signal. The same panels were probed with a β-actin specific probe as a positive control, and all tissues yielded a signal with this probe.

7.3. EXAMPLE 3
USE OF MOLECULES WHICH BIND SEQ ID NOS. 3–4.

Molecules which bind SEQ ID Nos. 3, 4,6 or amino acid residues 1–502 of SEQ ID NO: 4 will include, e.g., monoclonal antibodies and and other small molecules which act as blocking agents, or as activators. See above. These molecules are identified as agonists or antagonists of SEQ ID Nos. 3, 4, 6 or amino acid residues 1–502 of SEQ ID NO: 4 by the following types of assays. Tumor cell lines which are well known in the art, e.g., astrocytoma cell line 1321N1, are cultured in the presence of the binding molecules, and antagonist or agonist activity is identified by changes in the growth rate of the tumor cells. In one embodiment, the binding molecule is an antagonist which causes cell death.

Antibodies or other suitable binding molecules which bind to SEQ ID Nos, 3, 4, 6 or amino acid residues 1–502 of SEQ ID NO: 4 are also useful in receptor protein purification and for in situ hybridization analyses. Initial in situ analyses identify associations between the expression of SEQ ID Nos. 3, 4, 6 or amino acid residues 1–502 of SEQ ID NO: 4 and genetic disorders of the immune system or development. In situ hybridization with these binding molecules then diagnoses these genetic disorders of the immune system or development in patients.

7.4. EXAMPLE 4
SEQ ID NOS. 5 OR 23 AND 6 OR 24

SEQ ID NO. 5 (FIG. 4) is a 5' and 3' extension of the original cDNA sequence, SEQ ID NO. 2. In the 5' direction, additional sequence was obtained by a PCR based method of extending 5' sequence information from truncated cDNAs called 5' RACE (Rapid Amplification of cDNA Ends) (Frohman, M. A., Dush, M. K. and Martin, G. R., (1988) Proc. Natl. Acad. Sci. USA 85, 8998–9002). Fetal Liver Marathon-Ready cDNA (Clontech) was used as template for PCR reactions. Adaptor primer AP1 provided by Clontech was used as the 5' PCR primer, a gene-specific primer 10244-52 (5'-CTCATCCTCAAGCCCCTCTTT-3', SEQ ID NO: 12) was used as the 3' PCR primer. The products of this PCR reaction were diluted 100 fold and used as a template for a nested PCR reaction with API as the 5' primer and another gene specific primer 10244-51 (5'-CCATGAGAGTTCCCGCCTCTG-3', SEQ ID NO:13) as the 3' primer. The products of this PCR reaction were cloned into the pGEM®-T Easy vector using the pGEM®-T Easy Vector System (Promega) as instructed in the user manuel. Bacterial suspensions of individual colonies derived from this cloning reaction were used as template for PCR reactions using vector primers (T7: 5'-GTAATACGACTCACTATAGGG-3', SEQ ID NO:14, SP6: 5'-ATTTAGGTGACACTATAGAAGG-3', SEQ ID NO:15) to generate DNA fragments for sequencing reactions. Using the same primers as in the PCR reactions (T7 and SP6), these DNA fragments were sequenced using the BigDYE terminator (Perkin Elmer ABI) cycle sequencing reactions (Sanger dideoxy). 138 nucleotides are contiguous with the original cDNA sequence SEQ ID NO: 2 on the 5' end. Based on these additional sequences, two additional gene specific primers were designed (10244-A: 5'-CCCAGGCTGACGTGCCGATGC-3', SEQ ID NO:16; 10244-B: 5'-GCAGCAGGCCAGTTTAGTTCC-3', SEQ ID NO:17), and these were used to repeat the 5' RACE process.

Fetal Liver Marathon-Ready cDNA (Clontech) was used again as template for PCR reactions with primers AP1 and the gene-specific primer 10244-B. The products of this PCR reaction were used as a template for the nested PCR reaction wtih AP1 as the 5' primer and the gene specific primer 10244-A as the 3' primer. The products of this PCF reaction were similarly cloned into the pGEM®-T Easy vector and inserts of individual colonies were similarly sequenced. Additional nucleotide sequences were obtained from sequencing reactions that produced sequnces that are contiguous with the sequence obtained above to complete SEQ ID NO. 5 (2365 bp) as shown in FIG. 4.

SEQ ID NOS: 6 or 24 (FIG. 5) is the amino-acid translation from nucleotide 205 to 1866 of SEQ ID NOS: 5 or 23, including the starting methionine and stop codon. The first 21 amino-acids comprise the hydrophobic region that represents the signal peptide. EGF motifs are located at amino acid residues 80–93 of SEQ ID NOS: 6 or 24 (EGF motif 1), amino acid residues 95–128 of SEQ ID NOS: 6 or 24 (EGF motif 2), amino acid residues 133–168 of SEQ ID NOS: 6 or 24 (EGF motif 3), amino acid residues 175–214 of SEQ ID NOS: 6 or 24 (EGF motif 4), amino acid residues 220–259 (EGF motif 5). A hydrophobic region suggestive of a possible transmembrane domain is located at amino acid residues 446–465 of SEQ ID NOS: 6 or 24, two potential N-glycosylation sites at amino acid residues 247 and 346 of SEQ ID NOS: 6 or 24, a potential tyrosine phosphorylation site at amino acid residue 509 of SEQ ID NOS: 6 or 24, and a RGD motif at amino acid residues 363–365 of SEQ ID NOS: 6 or 24.

The presence of an RGD motif predicts an interaction with integrins. The putative tyrosine phosphorylation motif suggests, that the molecule might act as a kinase substrate, so that phosphorylation could be used to regulate ERHy1 expression or to modulate its function.

Further analysis of the deduced amino acid sequence of SEQ ID NOS: 6 or 24 using SignalP prediction (Nielsen et al., Protein Eng., 10:1–6 (1997)) indicated that an 18-amino acid putative signal peptide region is located at the N-terminus. Further analysis of the hydrophobic portions at the C-terminus by the TMHMM server indicated that these portions do not encode typical transmembrane domains. The presence of a signal peptide and the absence of a typical transmembrane domain suggests that this protein actually is secreted.

Thus, SEQ ID No. 1 encodes the polypeptide sequence of SEQ ID Nos. 3 which contains EGF motifs that are similar to the EGF motif of the drospophila developmental gene Notch (32% amino acid sequence homology), the EGF motif of CD97 (38% amino acid sequence homology), and the EGF consensus motif (26% amino acid homology). SEQ ID No 1 is an EST for a family member of the EGF-containing genes with most similarity to the EGF motifs of drosophila Notch and human CD97.

Likewise SEQ ID No. 5 encodes the polypeptide sequence of SEQ ID No. 6 which is similar in protein sequence to the EGF motif of the drospophila developmental gene Notch (31% amino acid sequence homology), the EGF motif of CD97 (34% amino acid sequence homology), and the EGF consensus motif (24% amino acid homology). The protein sequence also has homology to latent TGF (a protein implicated in osteoporosis).

In general, the content and position of certain highly conserved amino acid residues identifies SEQ ID No. 6 as a member of the EGF-repeat containing family (conserved amino acid residues are shown in FIG. 1). Six cysteines and two glycines are highly conserved among EGF-repeats which define an EGF motif. Four cysteines and one glycine are absolutely conserved in the consensus sequence from known EGF-repeat domains. The four and a half EGF motifs in SEQ ID No. 6 contain the cysteines and the one glycine residue with the appropriate spacing between these residues. Thus, SEQ ID No. 6 is properly classfied as a protein containing the EGF-repeat motif SEQ ID No. 6 has the highest amino acid similarity to CD97, but the conserved residues of the motif are most similar to drosophila Notch. As noted above, resequencing of plasmids pEGFR-HY2 and pEGFR-HY3 showed that a sequence error had been reported in SEQ ID NO: 5 and 6 which has been corrected in SEQ ID NOS: 23 and 24.

7.5. EXAMPLE 5
CHROMOSOMSL LOCALIZATION OF SEQ ID NOS: 5: OR 23 (ERy1)

The chromosomal location of ERHy1 was mapped as follows: PCR primers (5'-GTCATTTCTAATCTTTCCAC-3', SEQ ID NO: 19 and 5'-GAAATGTTGCAGAGAGAAGCTC-3', SEQ ID NO: 20) specific for the 3' untranslated region were used to screened against the NMGMS human/rodent somatic cell hybrid mapping panel #2 [Drwinga et al., Genomics, 16:311–314 (1993)]. This PCR yielded a 117-nucleotide product using the following conditions: initial denaturation for 2 min at 94° C. followed by 40 cycles of amplification at 94° C. for 30 sec., 54° C. for 1 min. and 72° C. for 1 min. The analysis revealed that ERHy1 localized to chromosome X. Interestingly, aberrations to chromosome X have been implicated in both meningiomas and lung tumors [Dave et al., Cancer Genet. Cytogenet., 87:35–38 (1996); Lekanne Deprez et al., J. Neuropathol. Exp. Neurol. 54:224–235 (1995); Amo-Takyi et al., Histopathology 34:163–169 (1999), all of which are incorporated by reference herein].

The present invention is not to be limited in scope by the exemplified embodiments which are intended as illustrations of single aspects of the invention, and compositions and methods which are functionally equivalent are within the scope of the invention. Indeed, numerous modifications and variations in the practice of the invention are expected to occur to those skilled in the art upon consideration of the present preferred embodiments. Consequently, the only limitations which should be placed upon the scope of the invention are those which appear in the appended claims.

All references cited within the body of the instant specification are hereby incorporated by reference in their entirety.

What is claimed is:

1. An antibody or fragment thereof that specifically binds a polypeptide consisting of the amino acid sequence of SEQ ID NO: 4.

2. An antibody or fragment thereof that specifically binds a polypeptide consisting of amino acids 1–502 of SEQ ID NO: 4.

3. An antibody or fragment thereof that specifically binds a polypeptide consisting of amino acid 42–250 of SEQ ID NO: 4.

4. An antibody or fragment thereof that specifically binds a fragment of SEQ ID NO: 4 comprising one or more EGF motif regions selected from the group consisting of amino acids 42–56 of SEQ ID NO: 4, amino acids 57–107 of SEQ ID NO: 4, amino acids 108–165 of SEQ ID NO: 4, amino acids 166–211 of SEQ ID NO: 4 and amino acids 212–250 of SEQ ID NO: 4.

5. The antibody or fragment of claim 4 that specifically binds a fragment of SEQ ID NO: 4 comprising amino acids 42–56 of SEQ ID NO: 4.

6. The antibody or fragment of claim 4 that specifically binds a fragment of SEQ ID NO: 4 comprising amino acids 57–107 of SEQ ID NO: 4.

7. The antibody or fragment of claim 4 that specifically binds a fragment of SEQ ID NO: 4 comprising amino acids 108–165 of SEQ ID NO: 4.

8. The antibody or fragment of claim 4 that specifically binds a fragment of SEQ ID NO: 4 comprising amino acids 166–211 of SEQ ID NO: 4.

9. The antibody or fragment of claim 4 that specifically binds a fragment of SEQ ID NO: 4 comprising amino acids 212–250 of SEQ ID NO: 4.

* * * * *